US011701257B2

United States Patent
Lavi et al.

(10) Patent No.: US 11,701,257 B2
(45) Date of Patent: Jul. 18, 2023

(54) DEVICE AND METHOD FOR CREATING A CHANNEL IN SOFT TISSUE

(71) Applicants: Sanoculis Ltd., Kiryat Ono (IL); Tel Hashomer Medical Research Infrastructure and Services Ltd., Ramat Gan (IL)

(72) Inventors: Gilad Lavi, Rishon Le'zion (IL); Yoseph Glovinsky, Petah Tiqwa (IL); Vadim Shmukler, Rishon Le'Zion (IL); Nir Israeli, Kiryat Ono (IL)

(73) Assignee: SANOCULIS LTD.

( * ) Notice: Subject to any disclaimer, the term of this patent is extended or adjusted under 35 U.S.C. 154(b) by 633 days.

(21) Appl. No.: 16/493,686

(22) PCT Filed: Apr. 9, 2018

(86) PCT No.: PCT/IL2018/050412
§ 371 (c)(1),
(2) Date: Sep. 12, 2019

(87) PCT Pub. No.: WO2018/189740
PCT Pub. Date: Oct. 18, 2018

(65) Prior Publication Data
US 2020/0129331 A1  Apr. 30, 2020

Related U.S. Application Data

(60) Provisional application No. 62/595,172, filed on Dec. 6, 2017.

(30) Foreign Application Priority Data

Apr. 9, 2017  (IL) .......................................... 251684

(51) Int. Cl.
*A61F 9/007*  (2006.01)

(52) U.S. Cl.
CPC ................................. *A61F 9/00763* (2013.01)

(58) Field of Classification Search
CPC .. A61F 9/00763; A61F 9/00781; A61F 9/007; A61F 9/013; A61B 10/0275;
(Continued)

(56) References Cited

U.S. PATENT DOCUMENTS 3,683,892 A  8/1972  Harris
3,732,858 A  5/1973  Banko
(Continued)

FOREIGN PATENT DOCUMENTS

CN  2262404  9/1997
CN  1218380 A  6/1999
(Continued)

OTHER PUBLICATIONS

Brown et al, "Internal sclerectomy with an automated trephine for advanced glaucoma" Ophthalmology, 1988; 95, 728-734.
(Continued)

*Primary Examiner* — Richard G Louis
*Assistant Examiner* — Chima U Igboko
(74) *Attorney, Agent, or Firm* — Isus Intellectual Property PLLC; Anthony Jason Mirabito

(57) ABSTRACT

Medical devices and methods for removing a predetermined shape of soft tissue from a target tissue layer, thereby leaving a matching channel with predetermined geometry and orientation in the target tissue layer, are described. The medical device comprises coaxial outer and inner elongated members extending along axis X; said outer member comprises an open distal side and a first distal part configured for sticking to said target tissue layer during forward axial movement; said inner member comprises a second distal part configured to rotate and project distally through said open distal side to cut said predetermined shape of the soft (Continued)

tissue from the target tissue layer and create said channel formed as a hole across the target tissue layer.

11 Claims, 26 Drawing Sheets

(58) Field of Classification Search
CPC ........ A61B 10/0266; A61B 2010/0208; A61B 2017/00345; A61M 27/002
See application file for complete search history.

(56) References Cited

U.S. PATENT DOCUMENTS

| | | | |
|---|---|---|---|
| 3,893,445 A * | 7/1975 | Hofsess | A61B 10/025 604/188 |
| 4,002,169 A | 1/1977 | Cupler | |
| 4,445,509 A | 5/1984 | Auth | |
| 4,699,154 A | 10/1987 | Lindgren | |
| 4,881,551 A | 11/1989 | Taylor | |
| 4,887,613 A | 12/1989 | Farr et al. | |
| 4,895,166 A | 1/1990 | Farr et al. | |
| 4,958,625 A | 9/1990 | Bates et al. | |
| 5,036,860 A | 8/1991 | Leigh et al. | |
| 5,263,974 A | 11/1993 | Matsutani et al. | |
| 5,324,300 A * | 6/1994 | Elias | A61B 10/025 606/179 |
| 5,474,532 A | 12/1995 | Steppe | |
| 5,487,725 A | 1/1996 | Peyman | |
| 5,634,918 A | 6/1997 | Richards | |
| 5,752,923 A | 5/1998 | Terwilliger | |
| 5,893,862 A | 4/1999 | Pratt et al. | |
| 5,968,058 A | 10/1999 | Richter et al. | |
| 6,083,176 A | 7/2000 | Terwilliger | |
| 6,083,177 A | 7/2000 | Kobren et al. | |
| 6,217,584 B1 | 4/2001 | Nun | |
| 6,361,504 B1 | 3/2002 | Shin | |
| 7,344,546 B2 | 3/2008 | Wulfman et al. | |
| 7,914,463 B2 | 3/2011 | Tarter et al. | |
| 8,038,692 B2 | 10/2011 | Valencia et al. | |
| 8,361,098 B2 | 1/2013 | Schachar et al. | |
| 2002/0095101 A1 | 7/2002 | Fontenot | |
| 2002/0120284 A1 | 8/2002 | Schachar et al. | |
| 2002/0120285 A1 | 8/2002 | Schachar et al. | |
| 2003/0004528 A1 | 1/2003 | Ishikawa | |
| 2003/0073929 A1 | 4/2003 | Baltschun et al. | |
| 2003/0225344 A1 | 12/2003 | Miller | |
| 2004/0006358 A1 | 1/2004 | Wulfman et al. | |
| 2004/0106948 A1 | 6/2004 | Cunningham | |
| 2004/0157428 A1 | 8/2004 | Quick et al. | |
| 2004/0167428 A1 | 8/2004 | Quick et al. | |
| 2005/0080441 A1 | 4/2005 | Dodge et al. | |
| 2005/0203441 A1 | 9/2005 | Voegele | |
| 2005/0245950 A1 | 11/2005 | Kozlowski | |
| 2006/0036269 A1 | 2/2006 | Schachar et al. | |
| 2006/0052722 A1 | 3/2006 | Brautigam et al. | |
| 2006/0100654 A1 | 6/2006 | Fukuda et al. | |
| 2006/0224084 A1 | 10/2006 | Vetter et al. | |
| 2006/0241580 A1 | 10/2006 | Mittelstein et al. | |
| 2007/0287551 A1 | 12/2007 | Wang et al. | |
| 2008/0234698 A1* | 9/2008 | Oostman | A61B 17/32053 606/133 |
| 2009/0018603 A1 | 1/2009 | Mitelberg et al. | |
| 2009/0024057 A1 | 1/2009 | Owen et al. | |
| 2009/0105651 A1 | 4/2009 | Wada et al. | |
| 2009/0112119 A1 | 4/2009 | Kim | |
| 2009/0204021 A1 | 8/2009 | Shabaz et al. | |
| 2009/0306657 A1 | 12/2009 | Svenden et al. | |
| 2009/0306691 A1 | 12/2009 | Cambronne et al. | |
| 2010/0146799 A1 | 6/2010 | Hoffman et al. | |
| 2010/0026214 A1 | 10/2010 | Siegel et al. | |
| 2010/0262147 A1 | 10/2010 | Siegal et al. | |
| 2011/0105944 A1 | 5/2011 | Ohnishi et al. | |
| 2011/0144671 A1 | 6/2011 | Svenden et al. | |
| 2011/0160740 A1 | 6/2011 | Makower et al. | |
| 2012/0245487 A1 | 12/2012 | Eells et al. | |
| 2014/0180321 A1 | 6/2014 | Dias et al. | |
| 2015/0011926 A1 | 1/2015 | Reitsamer et al. | |
| 2015/0141868 A1 | 5/2015 | Clark et al. | |
| 2015/0238687 A1 | 8/2015 | Novakovic et al. | |
| 2016/0007975 A1 | 1/2016 | Kim et al. | |
| 2016/0089180 A1 | 3/2016 | Entabi | |
| 2016/0249893 A1 | 9/2016 | Arnholt et al. | |

FOREIGN PATENT DOCUMENTS

| | | |
|---|---|---|
| CN | 1355716 A | 6/2002 |
| CN | 1387829 | 1/2003 |
| CN | 1882282 | 12/2006 |
| CN | 1976732 A | 6/2007 |
| CN | 101032419 | 9/2007 |
| CN | 200984221 | 12/2007 |
| CN | 201008575 | 1/2008 |
| CN | 201023367 Y | 2/2008 |
| CN | 101422385 | 5/2009 |
| CN | 101489634 A | 7/2009 |
| CN | 101507850 A | 8/2009 |
| CN | 102046102 A | 5/2011 |
| CN | 102056557 A | 5/2011 |
| CN | 202365865 | 8/2012 |
| CN | 103751889 A | 4/2014 |
| CN | 104582792 | 4/2015 |
| CN | 105073023 A | 11/2015 |
| CN | 105212981 A | 1/2016 |
| CN | 106264668 A | 1/2017 |
| CN | 104688303 B | 4/2017 |
| DE | 644490 C | 5/1937 |
| DE | 10223253 | 11/2002 |
| DE | 102007002855 | 12/2007 |
| EP | 0709063 A1 | 5/1996 |
| EP | 1695664 | 8/2006 |
| EP | 1815799 | 2/2007 |
| EP | 1875873 | 1/2008 |
| EP | 2039300 | 3/2009 |
| EP | 2907460 B1 | 9/2019 |
| JP | H0847505 A | 2/1996 |
| JP | H09504979 | 5/1997 |
| JP | H11155872 | 6/1999 |
| JP | 2003024339 | 1/2003 |
| JP | 2004524091 A | 8/2004 |
| JP | 2005509491 | 4/2005 |
| JP | 2005177302 | 7/2005 |
| JP | 10201764 | 8/2010 |
| JP | 4705201 | 3/2011 |
| JP | 4970488 B2 | 4/2012 |
| KR | 1020090118943 | 11/2009 |
| RU | 2054895 | 2/1996 |
| RU | 2160053 C2 | 12/2000 |
| RU | 2212848 | 9/2003 |
| RU | 89380 | 12/2009 |
| RU | 2385694 | 4/2010 |
| RU | 2572745 C2 | 1/2016 |
| SU | 567447 | 9/1977 |
| SU | 1456115 | 2/1989 |
| WO | 8303343 A1 | 10/1983 |
| WO | 9524858 | 9/1995 |
| WO | 0016832 A1 | 3/2000 |
| WO | 2003043549 | 5/2003 |
| WO | 04080345 | 9/2004 |
| WO | 2008115526 | 9/2008 |
| WO | 2009059236 | 5/2009 |
| WO | 2009079155 A3 | 12/2009 |
| WO | 10118172 | 10/2010 |
| WO | 2013186779 A2 | 12/2013 |
| WO | 2014050456 | 4/2014 |
| WO | 2015145444 A2 | 10/2015 |
| WO | 2016158073 A1 | 10/2016 |

OTHER PUBLICATIONS

Shihadeh, et al, "Rescue of failed filtering blebs with ab interno trephination" Cataract Refract Surg, 2006; 32, 918-922.
First Examination Report—Corresponding Indian Application No. 201947036685, dated Jan. 20, 2022, 9 pages.

(56) References Cited

OTHER PUBLICATIONS

Office Action—Corresponding Chinese Application No. 201880020473.4, dated Oct. 25, 2021, 6 pages.
Office Action—Corresponding Japanese Application No. 2020-504476, dated Apr. 5, 2022, 5 pages.
Office Action—corresponding Korean Application No. 10-2019-7028141, dated Nov. 21, 2022, 8 pages.

\* cited by examiner

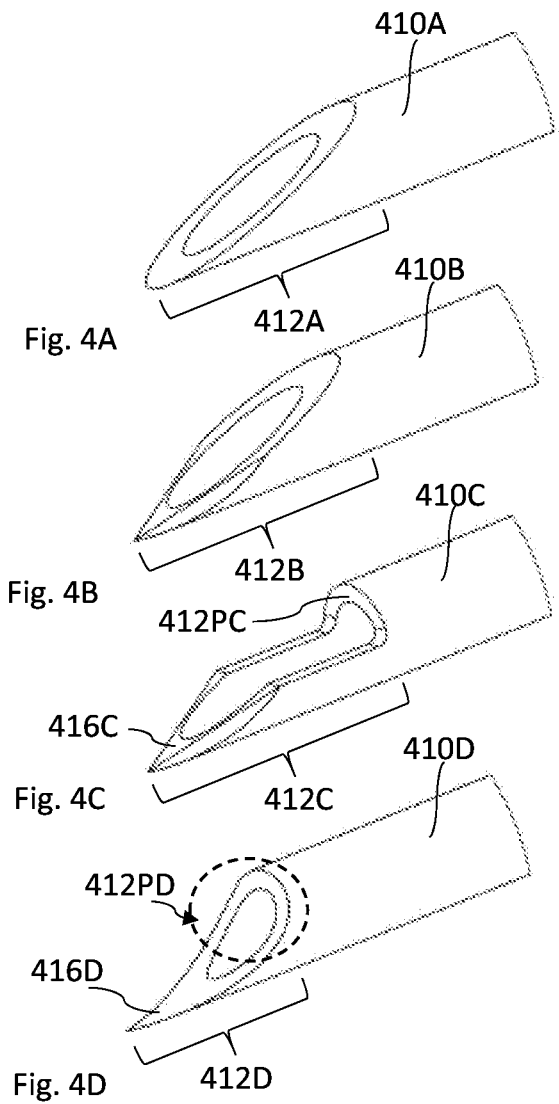

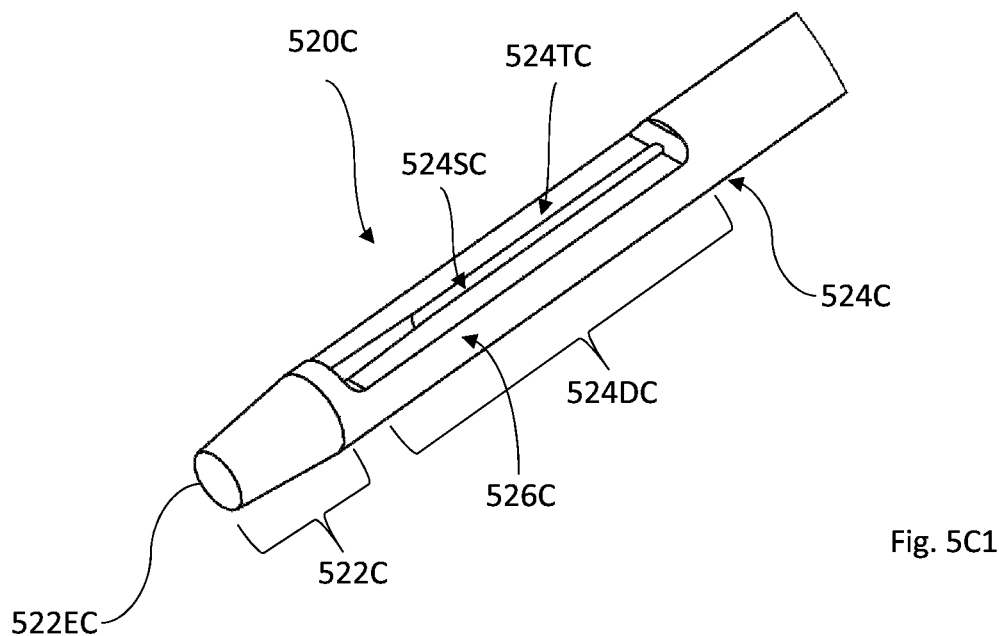
Fig. 5C1
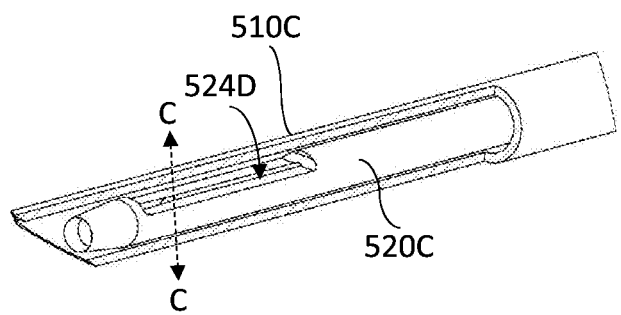
Fig. 5C2
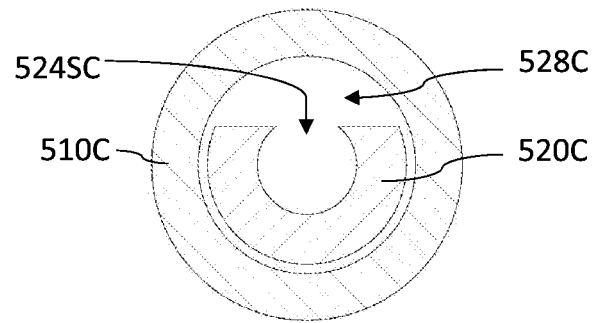
Fig. 5C3

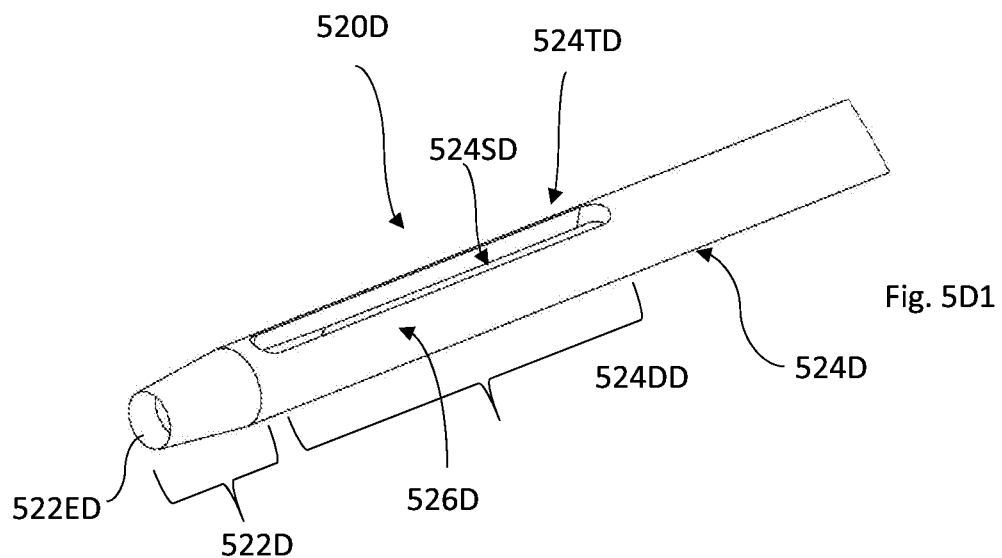
Fig. 5D1
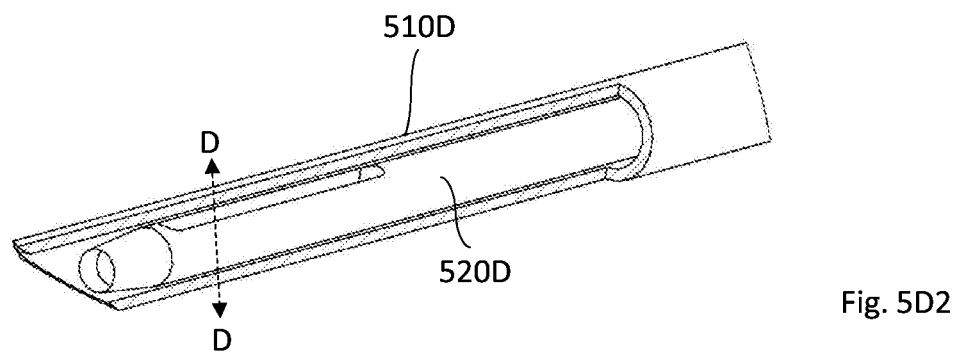
Fig. 5D2
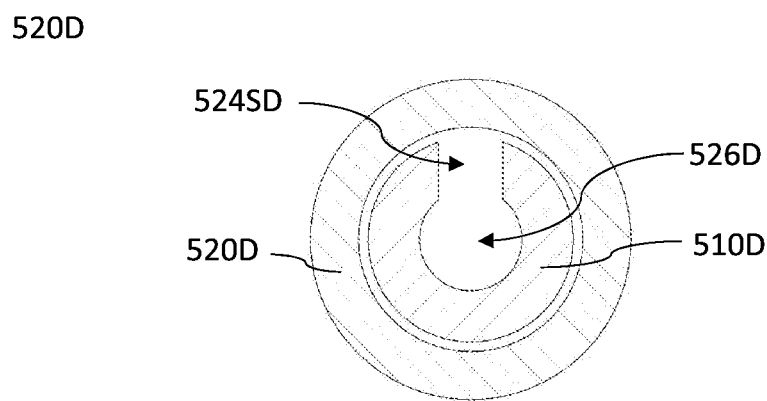
Fig. 5D3

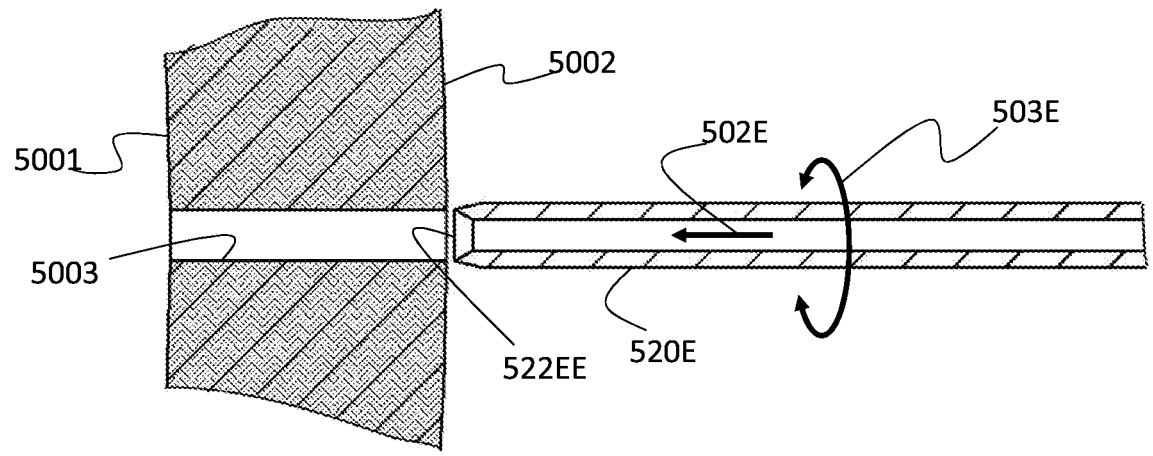
Fig. 5E1
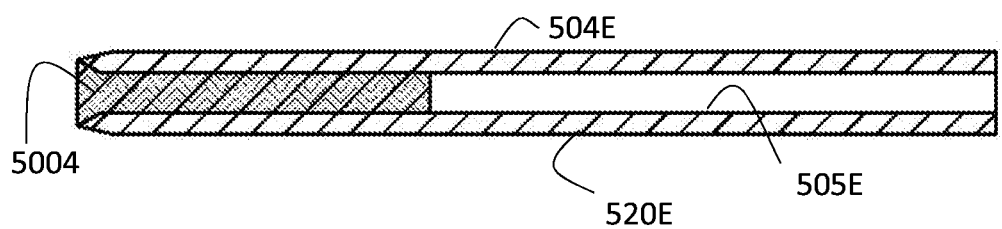
Fig. 5E2
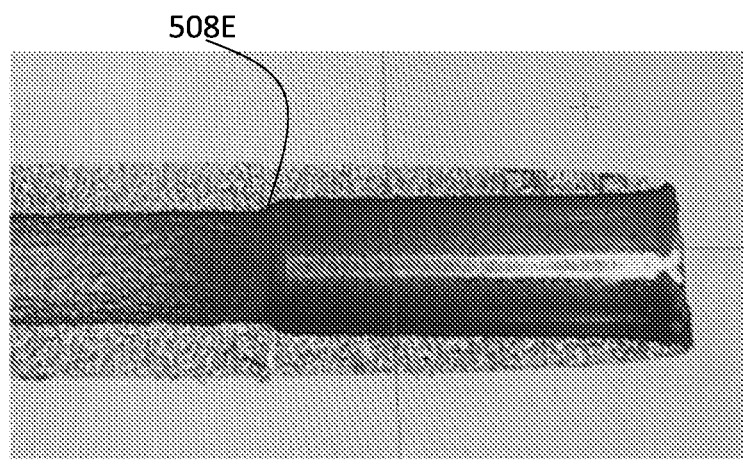
Fig. 5E3

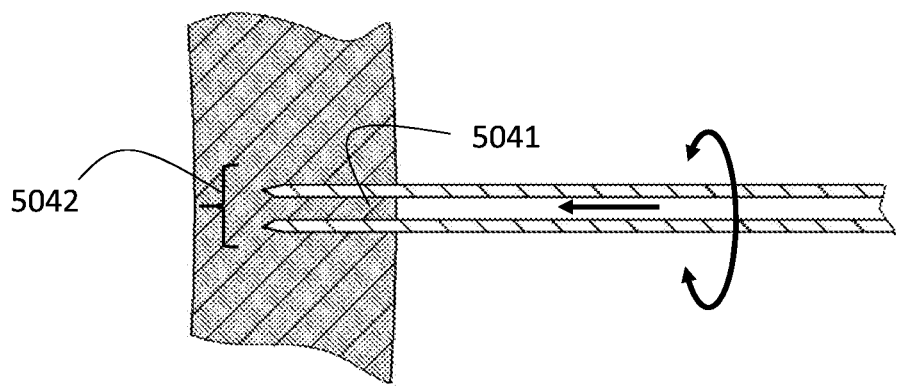
Fig. 5E4
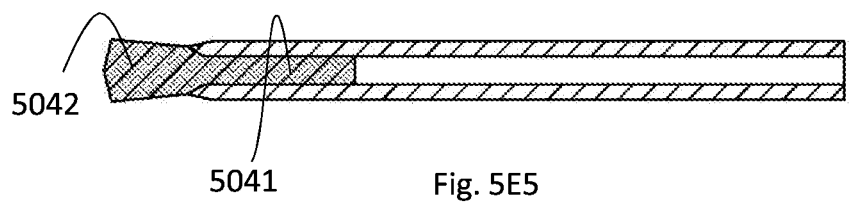
Fig. 5E5
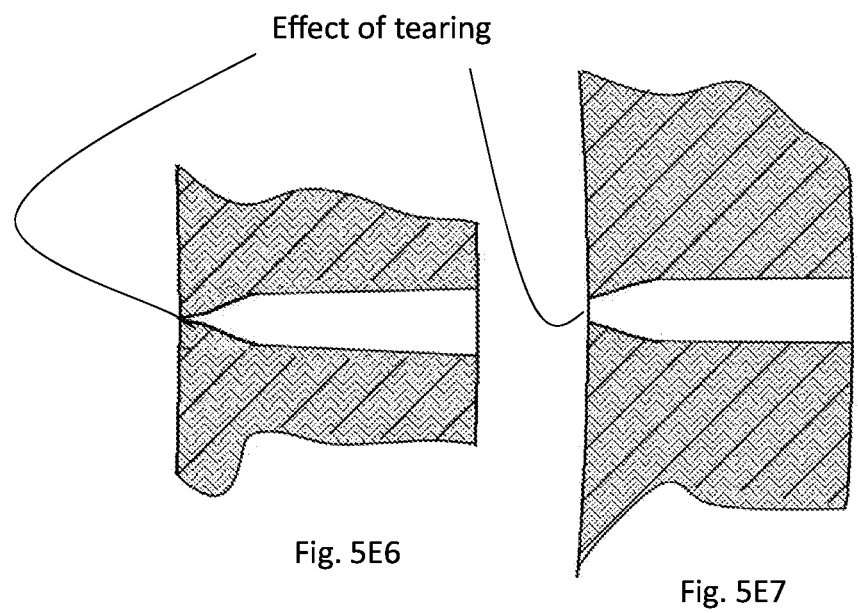
Fig. 5E6
Fig. 5E7

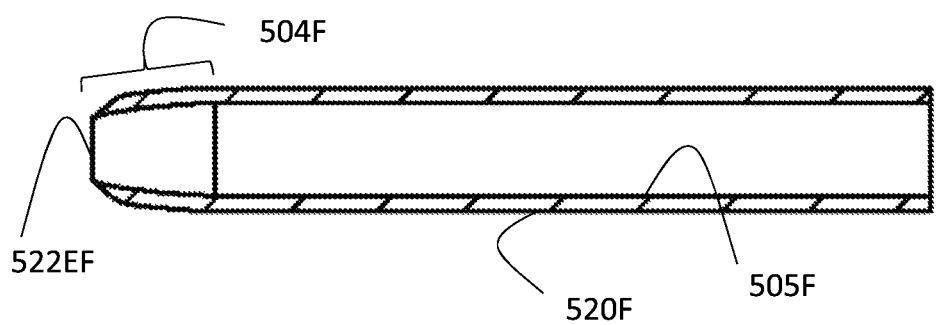
Fig. 5F
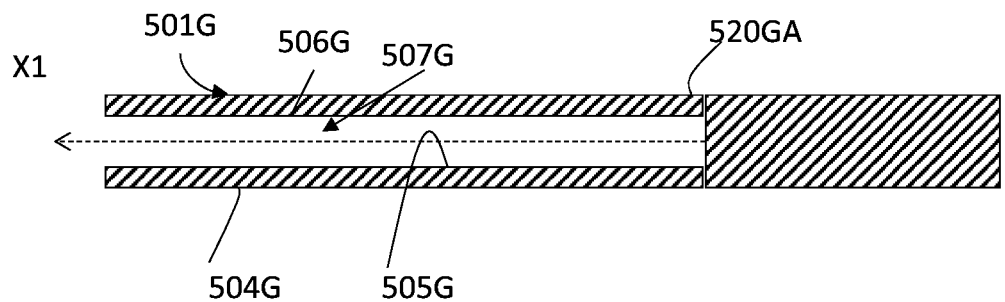
Fig. 5G1

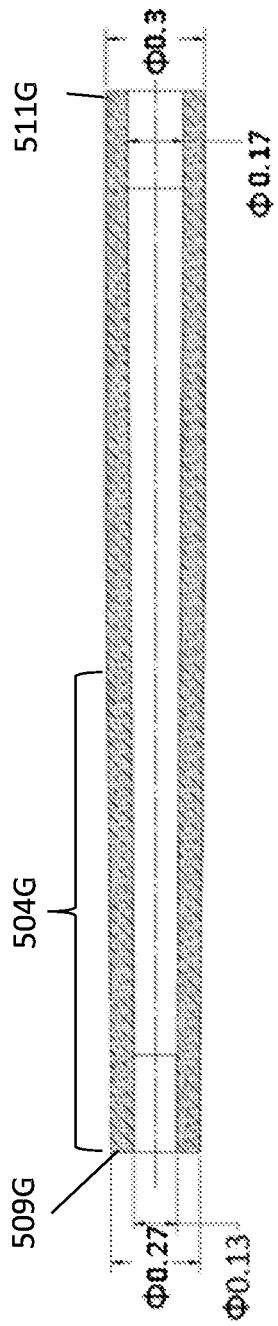
Fig. 5G2
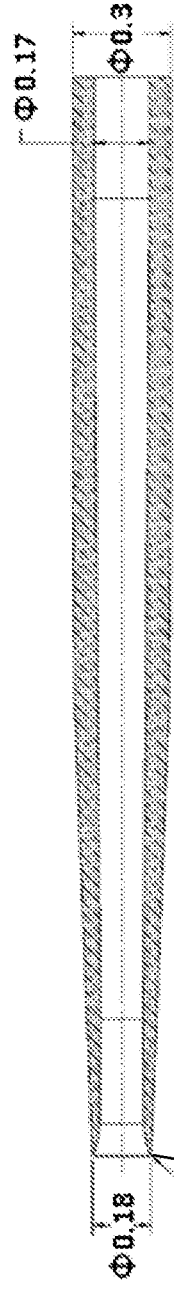
Fig. 5G3
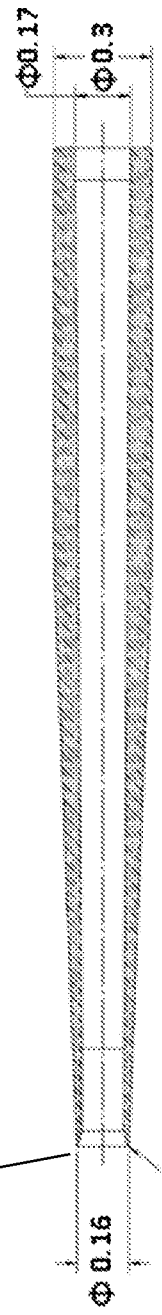
Fig. 5G4

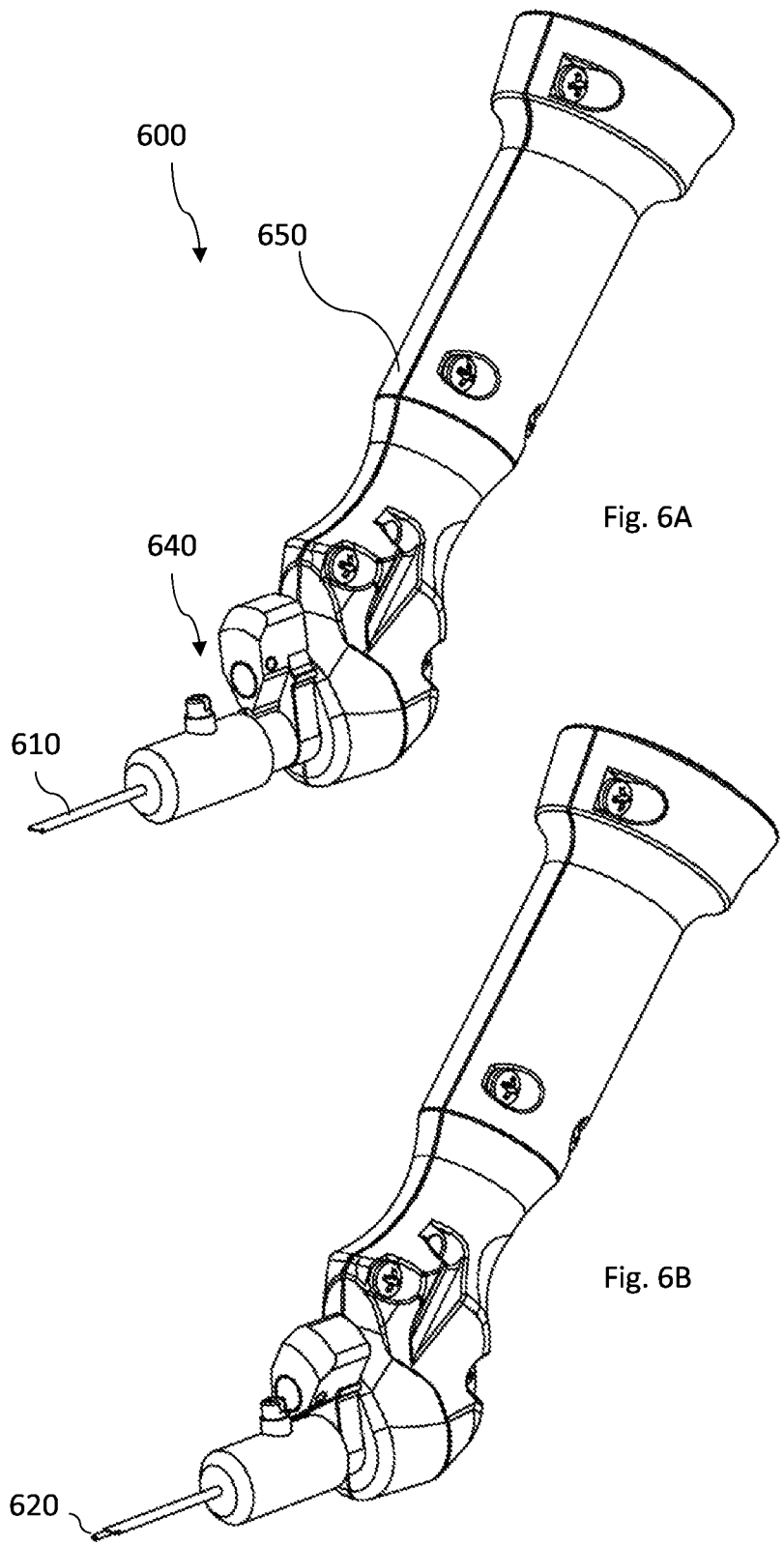

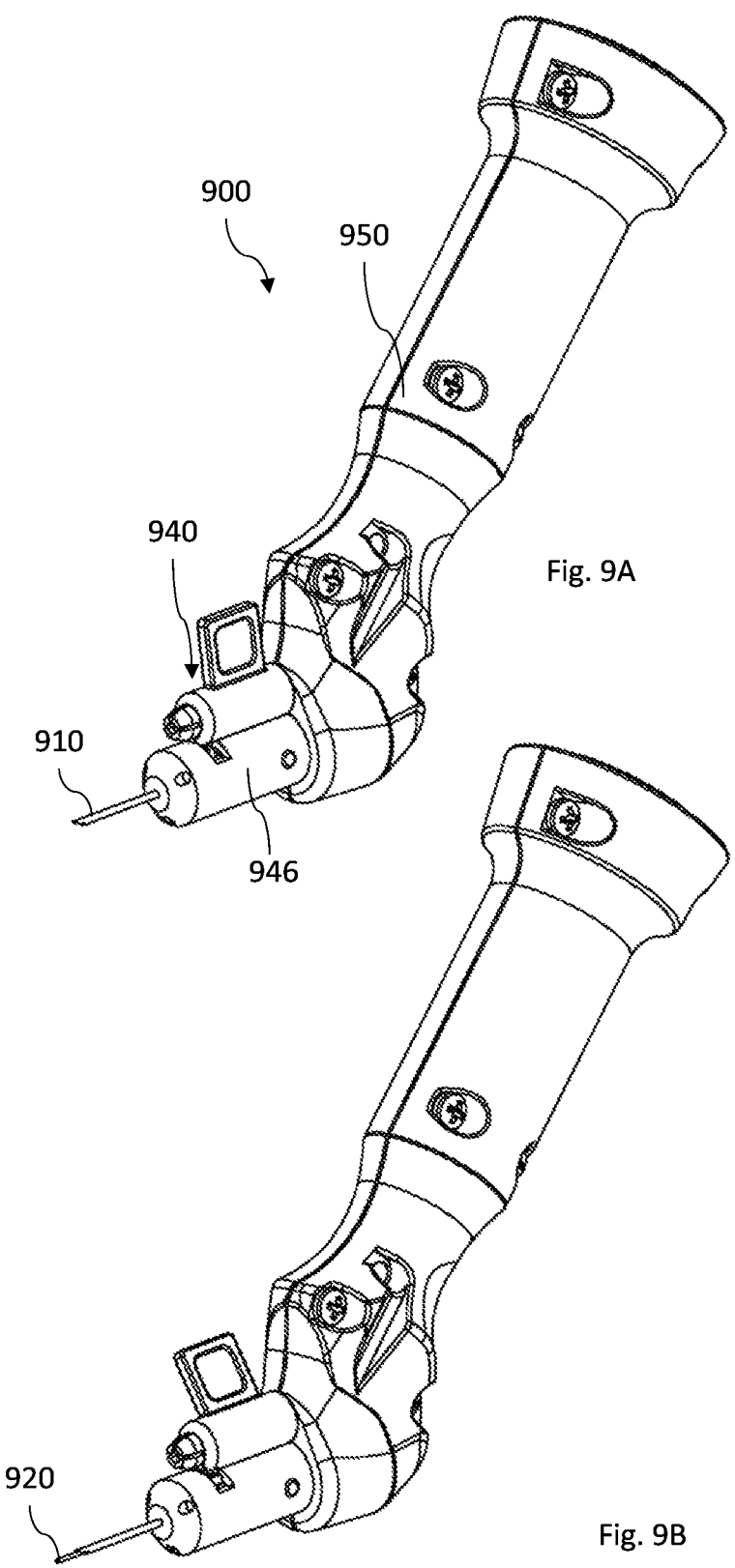

DEVICE AND METHOD FOR CREATING A CHANNEL IN SOFT TISSUE

TECHNOLOGICAL FIELD

The present invention is in the medical field and relates specifically to surgical devices, and more specifically to miniature surgical cuttings tools.

BACKGROUND

Removing tissue from the body is solicited in various scenarios including for diagnosis or treatment purposes. For example, in biopsy procedure, a sufficiently small tissue specimen is acquired in order to undergo examination outside the body. Usually, the shape of the specimen or the cavity left at the site of the removed tissue have low or no importance, the body heals from the injury leaving apparently no traces. In another example, tissue is removed in order to create paths for drainage of excessive liquids such as in Glaucoma condition (excessive intra ocular pressure).

Several surgical procedures are practiced to treat Glaucoma and/or elevated intraocular pressure (IOP). Filtering surgeries are used to gain access to the inner layers of the eye in order to create a drainage channel from the anterior chamber to the external surface of the eye under the conjunctiva, allowing aqueous humor to seep into a bleb from which it is slowly absorbed. Filtering surgeries are divided into either penetrating or non-penetrating types depending upon whether an intraoperative entry into the anterior chamber occurs. Scar formation at the site of operation may block aqueous humor circulation. Surgical adjuvants may be used to facilitate healthy tissue regeneration and keep created drainage channels functional.

Trephination to create ab interno sclerostomies was reported by Brown et al (Brown R H, Lynch M G, Denham D B, et al. Internal sclerectomy with an automated trephine for advanced glaucoma. Ophthalmology 1988; 95:728-734), and by SHIHADEH et al (Wisam A. Shihadeh, MD, Robert Ritch, MD, Jeffrey M. Liebmann, MD. Rescue of failed filtering blebs with ab interno trephination. Cataract Refract Surg 2006; 32:918-922), as a way of performing filtering procedures, after failure of other procedures due to blocking, while maintaining the integrity of the overlying conjunctiva at the treated site.

GENERAL DESCRIPTION

The present invention provides a novel technique for removal of tissue from the body. The technique of the present invention is particularly effective and useful in the controlled removal of soft tissue, e.g. by creating a well-defined, timely-controlled channel inside tissue. The technique of the present invention also provides for verifying the channel's creation and its dimensions, without a need for using external verification techniques such as imaging, by retrieving and preserving the shape of the tissue removed. It should be noted that a "channel" as used herein means a pathway created in the tissue after removal of a corresponding tissue piece from the body. No parts, such as implant(s), are left in the body to create or maintain the integrity of the channel. Other expressions that are used interchangeably herein are "hole", "void" and "pathway". Specifically, the unique technique allows for controllably creating a channel in one or more adjacent target tissue layers being part of a multilayered tissue structure while preserving the one or more tissue layers covering/preceding and/or following the target tissue layer(s). Further, the unique technique provides the user with on-line feedback referring the success of the channel creating procedure by verifying the removed tissue volume and shape. The length and/or the diameter, of the removed tissue (e.g. having a cylindrical shape) matches/indicates about the length and/or diameter of the created channel Minimizing the applied deformation on the removed tissue keeps it as close as possible to its original length and/or diameter, thereby providing improved and better real time feedback.

It is noted that the words "tissue layer" as used herein can mean a single tissue layer or a group of layers such as adjacent stacked layers (a multilayer) or a group of distinct layers. However, generally, the single tissue layer is the default meaning. Also, the "tissue layer" refers often to a tissue wall having a specific thickness and two sides (outer and inner, or proximal and distal) such that the channel/hole created therein extends between the two sides of the tissue wall.

For example, the channel may be a channel in the sclerocorneal junction of a subject's eye, which may be used to treat glaucoma by reducing intraocular pressure through providing fluid communication between the anterior chamber of the eye and the interface between the episclera and the conjunctiva tissues.

In the above-described literature (Brown et al and Shihadeh et al), the Ab interno trephination technique involve invasively introducing the surgical device into the anterior chamber of the eye through an incision made in the cornea opposite to the site of channel creation. This procedure is demanding, it depends heavily on the expertise of the surgeon and on the ability to accurately visualize the route of the surgical device inside the anterior chamber parallel to the iris into the filtration angle. It is also risky to vital organs such as the iris and lens as well as the angle structures that cannot be directly visualized unless an additional gonioscopic lens is used. This intraoperative gonioscopic lens is only rarely used even by glaucoma surgeons.

In contrast, the present invention provides a safe, minimally-invasive (Ab externo) and blazingly fast (in the order of seconds), highly-effective technique. As such, the present invention provides an opportunity for combined surgery by combining several surgical operations, for example combining treatment of high intraocular pressure according to the invention, together with cataract surgery, thus saving time and effort from both the surgeon and the patient.

Although, as described above, the present invention is advantageous in its Ab externo application, the device of the present invention can also be safely and effectively applied in Ab interno procedure, because as will be further detailed below, the device includes an outer part that functions as a protector that is configured to protect organs of the eye, including internal organs, such as the iris, when utilized in Ab interno configuration.

At different sites in the body, the target tissue in which the channel has to be made underlies or precedes other tissue(s). In such a situation, the challenge is even greater because harm to the surrounding tissue(s) or adjacent should be avoided. One example is creating a channel in the sclera while keeping the conjunctiva intact. The medical device of the present invention is configured, in the Ab externo application, to optimize the remote penetration through the outer, first, tissue (e.g., conjunctiva) followed by cutting inner, second, tissue (e.g., sclera) to form a channel, while the minimal force possible is applied, such that the hole created in the upper tissue (conjunctiva) heals almost immediately leaving no traces. On the other hand, in the Ab interno application, the device, while being actually inserted into the anterior chamber of the eye, its construction and way of action ensure that no harm is caused to other organs, including the outer conjunctiva, while it creates a channel in the sclera tissue from inside.

Further, the medical device of the present invention is configured for easy automatic or semi-automatic operation, relieving burden from surgeon and providing him continuous feedback over the whole surgical procedure. The technique of the present invention aids the surgeon in safe positioning of the device inside the tissue to be cut while still allowing him/her control over the channel's three-dimensional orientation.

Moreover, the device of the present invention may incorporate authentication or validation features by retaining form/specimen of tissue removed from the body during the channel creation. The shape of the cutting tool of the device also provides enhanced trapping of the removed tissue within the cutting tool and prevents or minimizes the chances of leaving the removed tissue within the tissue wall such as the eye wall.

The channel created by the technique of the present invention is advantageous, for example in comparison to other techniques that leave implant(s) inside the tissue so to insure the drainage of fluid, because nothing is left in the tissue, except for the created void/hole/channel extending between the two side walls of the specific target tissue layer or multilayer, as the case may be. In other words, the created channel is a hole through the tissue with no artificial tube/shunt left inside the target tissue at all. Therefore, the created channel can be dynamic acting as a pressure regulator, i.e. it can regulate its drainage capacity by changing its size based on the pressure acting on its both ends. When the pressure gradient increases the channel opens/increases its size accordingly, and when the pressure gradient decreases the channel closes/decreases its size accordingly.

The range of sizes of the channel can be controlled by the geometry and size of the device that creates the channel. In the specific example of creating a channel in the eye wall, to treat elevated IOP for example, the present invention is advantageous in achieving the channel creation and verification in the micro scale, as the desired dimensions of the drainage channel are typically about 0.1-0.2 mm in diameter and 1-1.5 mm in length, supposing a substantially cylindrical shape for the channel and the matching removed tissue. The present invention accomplishes the targets above in the micro level while overcoming the limitations of the currently available techniques. Inter alia, available techniques may be used to produce tools having tissue receiving cavities of up to about 0.5 mm length with the required above-mentioned diameter. However, this is not suitable for creating a substantially cylindrical channel within the eye wall that has a 1.5 mm length. The technique of the present invention enables creating cutting tools with micro-scale desired dimensions in diameter and length, thereby enabling to preserve the shape of the removed tissue to be used for verification of the channel creation.

Generally, the medical device of the present invention is configured to operate in three distinct phases, a positioning phase characterized by an essentially linear advancement of the device along its linear longitudinal axis through one or more tissue layers until reaching the target tissue and stabilizing there inside the target tissue by an anchoring/sticking portion of an outer part of the device, a channeling phase during which an inner rotatable cutting tool of the device is rotated around its linear longitudinal rotation axis and then advanced to project from the outer part of the device and progress inside the target tissue to cut tissue of the target tissue and create the channel with the desired dimensions (diameter, cross-section area, length . . . ), and a withdrawal phase in which the inner rotatable cutting tool is withdrawn from the target tissue into the outer part of the device and the whole device is retracted from the body. The withdrawal phase may be with or without rotation of the inner rotatable cutting tool depending, inter alia, on the tissue characteristics (kind, stiffness, region in the body), the time of operation and the desired channel shape. Typically, the outer part does not rotate during any of the phases and it only moves straight forwards and backwards on the linear longitudinal axis of the device. Generally, the outer part functions as a protective shaft, that protects the surrounding tissue during advancement of the device until reaching the target tissue, and as a stabilizing part such that its front (distal) portion is inserted/anchored/stuck in the target tissue to enable stable activation and performance of the inner rotatable cutting tool during the channeling phase.

Thus according to a broad aspect of the invention, there is provided a medical device for removing a predetermined shape of soft tissue from a target tissue layer thereby leaving a matching channel with predetermined geometry and orientation between two side walls of the target tissue layer, the device comprises coaxial outer and inner elongated members extending along axis X;

said outer member comprises an open distal side and a first distal part configured for sticking to said target tissue layer (or multilayer), during forward axial movement;

said inner member comprises a second distal part configured to rotate and project distally through said open distal side to said predetermined shape of the soft tissue from the target tissue layer and create said channel formed as a hole through the target tissue layer or multilayer.

In some embodiments, the first distal part is configured for penetrating at least one other tissue layer preceding the target tissue layer during the forward axial movement.

In some embodiments, the first distal part comprises a tissue piercing tip at its distal end configured and operable to penetrate said at least one other tissue layer and said target tissue layers and a proximal portion at its proximal side configured and operable to penetrate said at least one other tissue layer and to stop at said target tissue layer, thereby sticking said outer member in the target tissue layer.

In some embodiments, said first distal part has a mid-portion between said tip and said proximal portion having a shape and an orientation that complement a shape and an orientation of said second tissue layer.

In some embodiments, the first distal part has a predefined length such that said tip does not exit distally from said target tissue layer.

In some embodiments, the proximal portion is a rim of said outer member, formed by cutting a section of wall of the outer member along said axis X.

In some embodiments, the inner member is fixedly attached to and housed within said outer member during said forward axial movement of the outer member.

In some embodiments, the outer member is manually moved during said forward axial movement until its said sticking in the second tissue layer.

In some embodiments, the inner member, while rotating, is manually moved along said axis X to create the channel.

In some embodiments, the device comprises a constant-force moving mechanism configured and operable to move said inner member, while rotating, along said axis X under a constant force. In some other embodiments, the device comprises a constant rate moving mechanism configured and operable to move said inner member, while rotating, along said axis X with a constant rate.

In some embodiments, the device comprises an electric motor configured and operable for axially moving and/or rotating said inner member.

In some embodiments, the device comprises a cavity for collecting tissue cut from said target tissue layer during creation of said channel. In some embodiments, the cavity is located within said inner member. In some embodiments, the cavity is located in a space between said inner and outer members.

In some embodiments, the second distal part of said inner member is open at its distal end and comprises a round cutting edge configured to attach to and cut soft tissue while rotating. The inner member may comprise a chamber for retaining a full shape of tissue cut from said second tissue layer during creation of said channel.

In some embodiments, the inner member comprises:
- an elongated round body extending along a longitudinal axis and having a uniform outer diameter at a proximal side thereof,
- a cutting portion at a distal side of the elongated body, comprising at a distal end thereof a round cutting edge of a first diameter being smaller than said outer diameter and a distally and continuously decreasing outer diameter, and
- a cavity extending along the longitudinal axis inside the cutting tool from said cutting portion, the cavity having dimensions matching said soft tissue shape,
- wherein said tissue shape is cylindrical and has a length of about 1.5 mm and a diameter of between about 0.1 mm and about 0.2 mm.

In some embodiments, the inner member comprises:
- an elongated round body extending along a longitudinal axis and having a uniform outer diameter at a proximal side thereof,
- a cutting portion at a distal side of the elongated body, comprising at a distal end thereof a round cutting edge of a first diameter being smaller than said outer diameter and a distally and continuously decreasing outer diameter, and
- a cavity extending along the longitudinal axis inside the cutting tool from said cutting portion, the cavity having a length of at least the length of the removed tissue,
- wherein said cavity has a cavity diameter smaller than said first diameter at a distal end of the cavity and which increases continuously towards a proximal end of the cavity.

In some embodiments, the inner member comprises:
- an elongated round body extending along a longitudinal axis and having a uniform outer diameter at a proximal side thereof,
- a cutting portion at a distal side of the elongated body, comprising at a distal end thereof a round cutting edge of a first diameter being smaller than said outer diameter and a distally and continuously decreasing diameter, and
- a cavity extending along the longitudinal axis inside the cutting tool from said cutting portion, the cavity having a length of at least the length of the removed tissue,
- wherein said cavity has a constant cavity diameter being equal to said first diameter, and wherein said first diameter is between about 0.1 mm to about 0.2 mm.

In some embodiments, the inner member comprises a tissue trapper comprising a slit formed in a wall of the body of the inner member along at least part of said cavity. In some embodiments, the slit is formed by tangential cutting of the wall of the body of the inner member, said device thereby further comprising an outer cavity located between the inner and outer members. In some embodiments, the slit is formed by radial cutting of the wall of the inner member.

In some embodiments, the second distal part of said inner member is configured as a drill bit configured for removing soft tissue.

In some embodiments, the rotating of said second distal part comprises clockwise and anti-clockwise reciprocal movement.

In some embodiments, the tissue piercing tip is configured as a lancet.

In some embodiments, the first distal part of the outer member is formed by cutting the outer member in the direction of the axis X along a curved line chosen to provide smooth penetration, at a distal segment of the first distal part, with increasing resistance-to-progression force, at a proximal segment of the first distal part.

In some embodiments, the at least one other tissue layer comprises the conjunctiva and/or the tenon and said target tissue layer is the episclera and/or the sclera and/or the cornea of an eye.

In some embodiments, the predetermined geometry of the channel is selected to enable pressure regulation of a treated eye over a predetermined time period.

According to yet another broad aspect of the invention, there is provided a method for producing a cutting tool used in cutting soft tissue, the cutting tool comprising a distal cutting portion having at a distal end thereof a round cutting edge of a first diameter and a cavity extending for a predetermined length along a longitudinal axis of the cutting tool from said cutting portion and comprising a cavity diameter being either constant or increasing proximally along the predetermined length, the method comprising:
- providing a tool comprising at a distal side thereof a hollow cylinder having uniform outer and inner diameters and extending along at least said predetermined length, wherein said inner diameter is larger than said first diameter,
- shaping a distal portion of the hollow cylinder with a predetermined pattern such that both said inner and outer diameters decrease towards a distal end of the hollow cylinder and such that said first diameter is larger than said inner diameter and is smaller than said outer diameter at the distal end, and
- removing a slice of the hollow cylinder along said distal portion, such that the inner diameter at the distal end is substantially equal to said first diameter and the inner diameter at a proximal end of the distal portion is substantially equal to said cavity diameter.

In some embodiments, said shaping of the distal portion is carried out by swaging and/or spinning technique(s).

In some embodiments, said shaping of the distal portion is carried out by tapering technique.

In some embodiments, said predetermined pattern is linear.

In some embodiments, said predetermined pattern is non-linear.

In some embodiments, said cavity diameter is equal to said first diameter.

In some embodiments, the method further comprising: sharpening said round cutting edge from an internal side of the cutting portion, thereby providing that the cavity diameter at a proximal end of the cutting portion being smaller than the first diameter. In some embodiments, said cavity diameter increases proximally.

In some embodiments, the method further comprising coating an inner surface of said cavity with a friction-lowering composition.

In some embodiments, said predetermined length is at least 1.5 mm.

In some embodiments, said cavity diameter at a proximal side of the cavity is between 0.1 mm and 0.2 mm.

In some embodiments, said uniform outer and inner diameters of the hollow cylinder are about 0.3 mm and 0.16 mm respectively.

In some embodiments, after shaping, said outer and inner diameters of the hollow cylinder at the distal end are about 0.27 mm and 0.13 mm respectively.

In some embodiments, said distal portion of the hollow cylinder has a length along the longitudinal axis of between about 1 mm to about 2 mm.

According to yet another aspect of the present invention, there is provided a cutting tool for removing a predetermined shape of soft tissue while revolving and progressing, thereby leaving a matching channel between two walls of the soft tissue, the cutting tool being produced according to the method described above.

According to yet another broad aspect of the invention there is provided a method for creating a channel with predetermined geometry in a target tissue layer, the channel being formed as a hole extending between two side walls of the tissue layer, the method comprising:

providing a device comprising coaxial outer member comprising a first distal part configured for sticking to said tissue layer during forward axial movement and inner member comprising a second distal part configured to cut and remove tissue to thereby create said channel;

positioning said device at the target tissue layer by progressing the device along an axis X while said inner member is located inside said outer member until reaching said target tissue layer where the first distal part of the outer member is pushed into the target tissue such that at least a distal portion of the distal part is stuck inside the target tissue layer;

creating said channel by rotating and projecting said second distal part from said outer member to thereby cut and remove tissue from said target tissue layer and store the removed tissue in the device;

retracting said second distal part proximally out of said target tissue layer and into the inside of the outer member; and pulling the first distal part proximally out of said target tissue layer and withdrawing the device out of the body substantially along the axis X.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 4A-4D illustrate non-limiting examples of a part of a device according to exemplary embodiments of the invention;

FIGS. 5A-5D3 illustrate non-limiting examples of a part of a device according to the invention;

FIGS. 5E1-5E7—illustrate one non-limiting scenario of creating a channel in soft tissue and specifically in the eye wall;

FIGS. 5F-5G4 illustrate non-limiting examples of a device and methods for producing the device according to exemplary embodiments of the invention;

FIGS. 6A-6D illustrate a non-limiting example of a manual movement mechanism according to the invention;

FIGS. 9A-9E illustrate a non-limiting example of automatic movement mechanism according to the invention.

DETAILED DESCRIPTION OF EMBODIMENTS

The present invention provides a technique for creating a well-defined channel in a soft tissue. In one aspect, a medical device for removing a predetermined shape of soft tissue from a target tissue layer (or a first group of target tissue layers) thereby leaving a matching/corresponding channel with predetermined geometry and/or orientation through/between two side walls of the target tissue layer is provided. In some embodiments, such a device can be particularly useful in creating a drainage channel along the whole thickness of the episclera and/or sclera and/or cornea tissue (which will be generally referred to herein, for simplicity, as the sclera), of the eye to thereby treat excessive intraocular pressure. The sclera is covered by the conjunctiva and tenon tissues, such that approaching the sclera from outside requires penetrating the conjunctiva and the tenon. Therefore, the device may be also configured to penetrate through the conjunctiva/tenon before reaching the sclera.

Figure 1A:
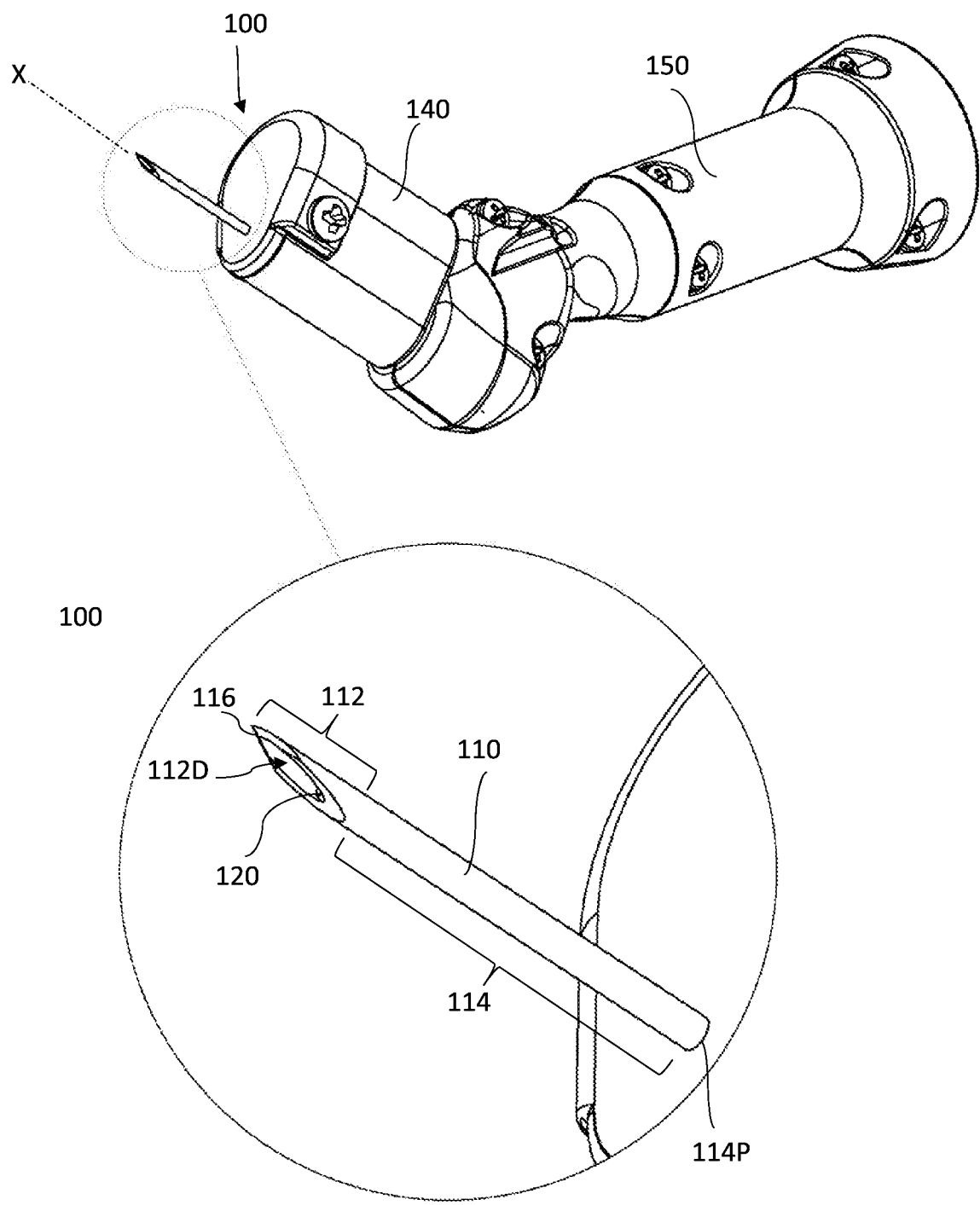
FIGS. 1A-1B illustrate a non-limiting exemplary embodiment of a device according to the invention.
Figure 1B:
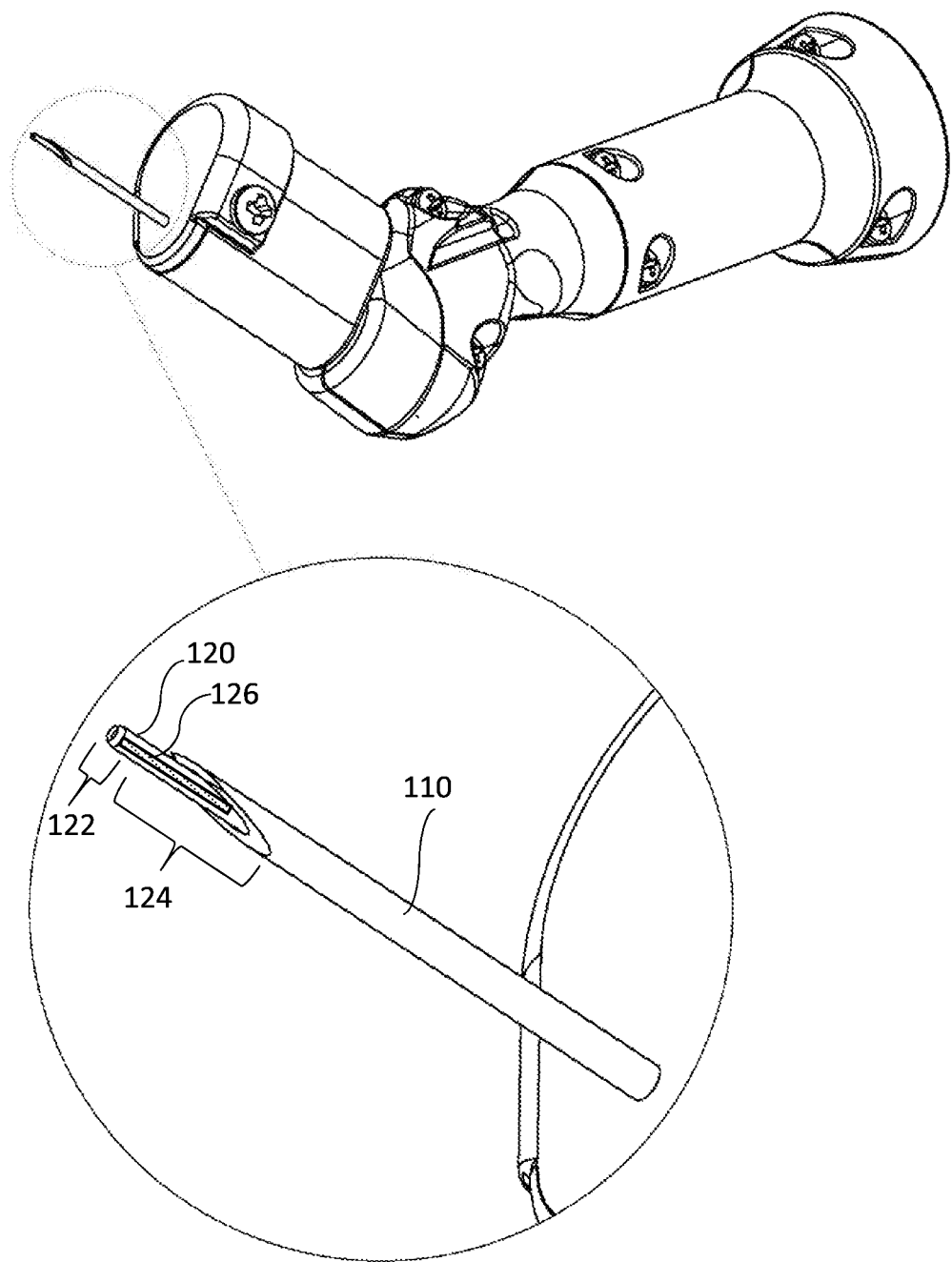

Reference is made to FIGS. 1A and 1B showing a specific, non-limiting, example of a medical device 100 according to some embodiments of the present invention.

The medical device 100 is configured for and capable of penetrating through first, upper, tissue layer(s) and creating a channel with predetermined geometry through a consecutive second, lower, target tissue layer. The device 100 includes coaxial outer and inner members, 110 and 120 respectively, extending along axis X, for creating the channel in the target tissue, and possibly penetrating the tissue layer(s) preceding the target tissue layer. The axis X is typically a longitudinal straight axis. The coaxial outer and inner members 110 and 120 are usually made from a hard, tough, material and are therefore rigid and do not bend when pushed/inserted/progressed through at least soft tissue. The coaxial outer and inner members 110 and 120 are mounted, at a proximal side 114P thereof, on a handle/gripping unit 150 by which the user holds/grips the device 100 and operates it.

The outer member 110 includes an open distal side 112D, a first distal part 112, and a first proximal elongated part 114. It is noted that the relative expressions "proximal" and "distal" as used herein, define relative orientation with respect to the user, such that "proximal" denotes the close side to the user and "distal" denotes the far side from the user. The outer member 110 is configured to move axially along the axis X to thereby penetrate soft tissue by its first distal part 112. The axial movement of the outer member 110 is achieved by user manual operation. As it is manually operated by the user, the outer member 110 can be fixedly/firmly attached, at the proximal side 114P, to the handle 150. Alternatively, it can be configured for manual sliding by the user along axis X while not being firmly attached to the handle 150. Details about the moving mechanism are described herein further below.

The first distal part 112 is configured for penetrating and passing through the tissue layer(s) preceding the target tissue layer, if any, during forward axial movement, and therefore it includes a tissue piercing tip 116, at the distal end of the first distal part 112, that enables the penetration. It is noted that, as the forward axial movement is manually controlled, the penetration of the preceding tissue layer(s), such as the relatively thin conjunctiva, is enabled by the manual pushing force applied by the user and which can be further facilitated by the manual lifting/pulling of the conjunctiva outwardly towards the user. The first distal part 112 is also configured to pierce the target, typically thicker, tissue layer, and stick into the target tissue layer so as to position the device inside the target tissue in which the channel is to be created, and provide the user with a pivotal point to define the three dimensional orientation of the channel. In addition to its plain name, the first distal part 112 is interchangeably called herein as "sticking part", "stabilizing part" or "anchoring part". It should be understood that while the first distal part 112 enters into the target tissue and sticks/anchors therein, it can be withdrawn backwardly by the application of a minimal force and without causing damage to the surrounding tissue. Sticking and/or anchoring as used herein do not mean a permanent state but rather a temporal, transitional state of the position of the first distal part, that gives the user a stable pivotal point of action.

The tissue piercing tip 116, formed at the most distal part of the first distal part 112, can be configured according to the known in the art, e.g. as done with conventional medical needles. Accordingly, the tissue piercing tip 116 can include, for example, a beveled lancet structure. Yet, it can have other configurations, as will be further described below with reference to FIGS. 4A to 4D.

The first proximal elongated part 114 is hollow, e.g. a hollow tube, enclosing and housing the inner member 120 there inside. Typically, the first proximal elongated part 114 has a cylindrical shape with a circular (round) or substantially circular transverse outer cross section. The first proximal elongated part 114 is configured to penetrate soft tissue smoothly and easily with minimum force, therefore it can have circular outer cross section and can be provided with a smooth (polished) outer surface to minimize friction during penetration into tissue. The inner cross section of the first proximal elongated part 114 is circular or has other shape that matches the outer surface of the inner member 120 enclosed therein.

The inner member 120 includes a second distal part 122 and a second proximal elongated part 124. The second distal part 122 is configured to project distally through the open distal side 112D, approaching the target tissue while rotating, to thereby cut a predetermined shape of the target tissue and create the channel with the predetermined geometry and orientation in the target tissue, while the first distal part 112 is substantially positioned inside the target tissue as described above and as will be further exemplified below with reference to FIGS. 3A to 3I. In general, the second distal part 122, at its distal end, is configured to provide effective attachment to the target tissue and to cut the target tissue while rotating. To this end, the distal end of the second distal part 122 can be provided with a cutting edge, a punching mechanism and the like, as will be further described below.

Generally, the device 100 includes a cavity/chamber 126 configured to collect the removed tissue therein, such that no tissue is left in the body. In some embodiments, the cavity/chamber is located inside the second proximal elongated part 124, as exemplified in FIG. 1B. In some other embodiments, the cavity/chamber 126 can be located in a space between the outer and inner members 110 and 120.

The device 100, including the handle 150 may be configured for single use, being disposable, therefore enhancing and maintaining safety and sterility of the device. The handle 150 can be configured as described in PCT/IL2016/051063 assigned to the assignee of the present invention.

The moving mechanism 140 is configured to enable axial movement of the outer member 110, forwards (distally) and backwards (proximally), and both axial and rotational movement of the inner member 120. The moving mechanism 140 can have manual (by the user) and/or automatic (by the use of mechanical and/or electrical means, such as a spring and/or a motor) operational modes for each of the movements it is capable of. The rotational movement of the inner member 120 can be in full or partial circles or rounds, clockwise and/or anticlockwise, and/or in reciprocal movement.

The construction and dimensions of the device can be costumed to match the application, the tissue properties, and anatomy and morphology of the site of body in which the channel is created.

For example, if used to create a drainage channel in the human eye, the dimensions of the device can be as follows:

The external diameter of the outer member is chosen to enable smooth and safe penetration into and withdrawal from tissue, while maintaining a minimal strength such that it does not break in the tissue during operation. It can be about 0.4-1.2 mm.

The overall length of the outer member is chosen to enable easy and safe access to the surgery site. It can be about 8-30 mm.

The length of the first distal part of the outer member can be chosen to enable insertion/sticking/anchoring of the first distal part into the second tissue, i.e. the sclera in this instance, while assuring that the first distal part does not protrude distally from the sclera, thus minimizing or cancelling invasive entrance into the anterior chamber of the eye. It can be about 0.5-3 mm.

The external diameter of the inner member is chosen to create the predetermined geometry of the channel, while maintaining a minimal strength such that it does not break in the tissue during operation. It can be about 0.2-0.5 mm.

The overall length of the inner member is chosen to enable its connection to a moving mechanism at the proximal side while providing sufficient forward distance to create the desired channel length. It can be about 15-40 mm.

The length of the second distal part of the inner member depends on the second distal part's specific construction that insures the channel creation.

During the channel creation, the inner member protrudes/projects from the outer member by about 1-4 mm.

The inner member's rotation can be in the range of about 1-10,000 rpm. And, the penetration force is about 0.2-10 Newton.

The resulting channel's diameter would be about 0.1-0.5 mm.

Figure 2A:
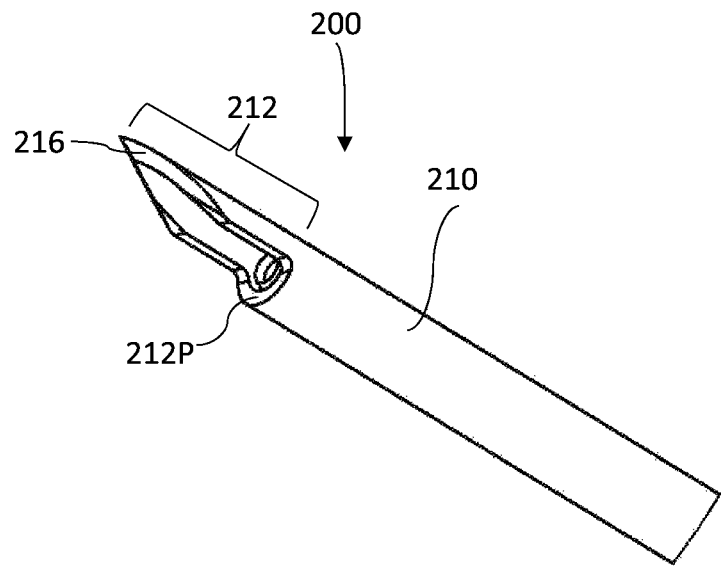
FIGS. 2A-2B illustrate another non-limiting exemplary embodiment of a device according to the invention.
Figure 2B:
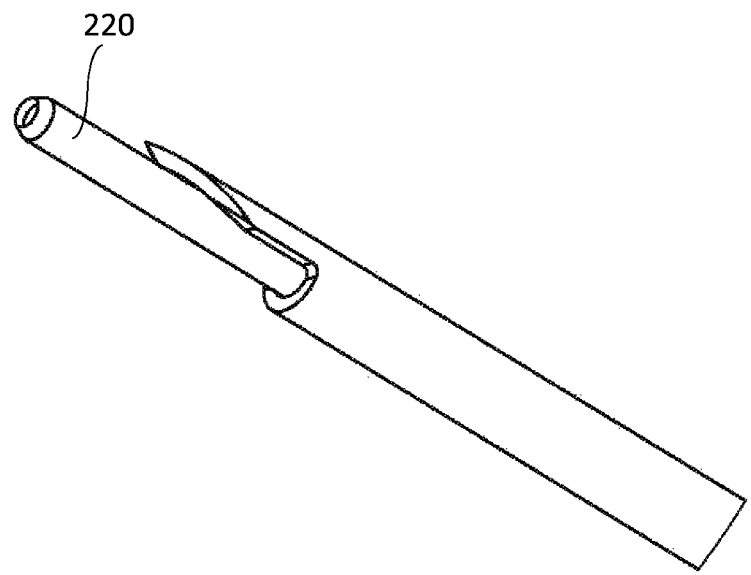

Reference is made to FIGS. 2A and 2B. Throughout the text, functional parts which have the same functionality, have the same numbers with difference of one hundred duplicates. For example, the number 210 denotes an outer member and the number 220 denotes an inner member, both configured as at least having the features described above with respect to outer member 110 and inner member 120, with possibly additional features. In the following various non-limiting embodiments of the device, including its outer and inner members and its moving mechanism will be exemplified. It should be understood, that any combination of one outer member, one inner member and one moving mechanism is equally possible. The shown or described specific examples should not limit the broad aspects of the invention.

FIGS. 2A and 2B exemplify a non-limiting example of the device 200 of the invention. In the figures, an outer member 210 and inner member 220 of the device 200 are shown. The outer member 210 and the inner member 220 are configured and operable at least as the outer member 110 and inner member 120 described above. FIG. 2A (as well as FIG. 1A) illustrates the device during the positioning phase, i.e. during inserting the device through the first and second (target) consecutive tissues, in which the outer member 210 leads the device into its position inside the second tissue to be channeled, and the inner member 220 (as well as 110 in FIG. 1A) is housed entirely in the outer member 210. FIG. 2B (as well as FIG. 1B) illustrates the device during the channeling phase, i.e. during creation of the channel by the rotational and forward movement(s), projection, of the inner member 220. As shown, the first distal part 212 of the outer member 210 includes a piercing portion/tip 216 at its most distal side, being configured as described above and operable to pierce and penetrate through tissue layer(s) preceding the target tissue, and to pierce, without fully penetrating, the target tissue layer. In addition, the first distal part 212 includes a portion 212P at its proximal side configured and operable to pierce and penetrate the tissue layer(s) preceding the target tissue layer and to stop at the second (target) tissue layer, i.e. the portion 212P prevents the outer member 210 from excessively penetrating the second (target) tissue in which the channel is created thereby sticking the outer member 210, by its distal piercing portion 216, in the target tissue layer. The portion 212P is interchangeably called herein as "stopping portion" or "stopper".

In the described example, the stopper 212P is an integral portion of the outer member 210 formed by a rim of the transverse, round, cross section of the outer member 210 by cutting a section of wall of the outer member 210 substantially along the axis X. Specifically, the section cut is a wall of the cylinder of the outer member 210, e.g. half of the cylinder of the outer member between its most distal end and up to a proximal point along the outer member. The length of the wall section cut along axis X defines the length of the first distal portion 212 and the latter defines the extent of sticking the outer member 210 into the target tissue such that the distal end of the piercing tip 216 does not protrude/exit distally from the target tissue layer.

Reference is made to FIGS. 3A to 3I exemplifying non-limiting techniques for creating a channel in soft tissue by using the medical device of the invention. The described example relates to creating a channel in the sclera tissue of the eye. However, as has already been said, the invention is not limited to this application and can be practiced at other regions in the body where creation of a controlled channel in a tissue layer preceding/beneath other tissue layer(s) is needed. Specifically, the invention enables channel creation at a region in the body which needs a clear and defined stopping/localization/stabilization feature of the device therein because the region cannot provide this feature; such a region is the soft tissue. The example described in FIGS. 3A to 3E relates to Ab externo procedure where the device approaches the sclera tissue from outside. A human eye 360 is shown, where a channel should be created at the region of the sclera-corneal junction 362. The created channel will controllably connect between the anterior chamber 364 of the eye and the sub conjunctival space/zone and hence allow the extra fluid accumulated in the anterior chamber to exit and by this reduce the intraocular pressure. As has been described earlier, the channel size can be controlled by providing a device with specific geometrical dimensions. Also, when used for treating excessive pressure, the size of the created channel is determined based on the magnitude of excessive pressure that should be treated. Higher pressure requires bigger channel and vice versa. The created channel insures effective regulation of pressure such that it expands or contracts between controlled sizes based on the pressure gradient across the channel, i.e. the pressure difference between inside and outside the eye.

Figure 3A:
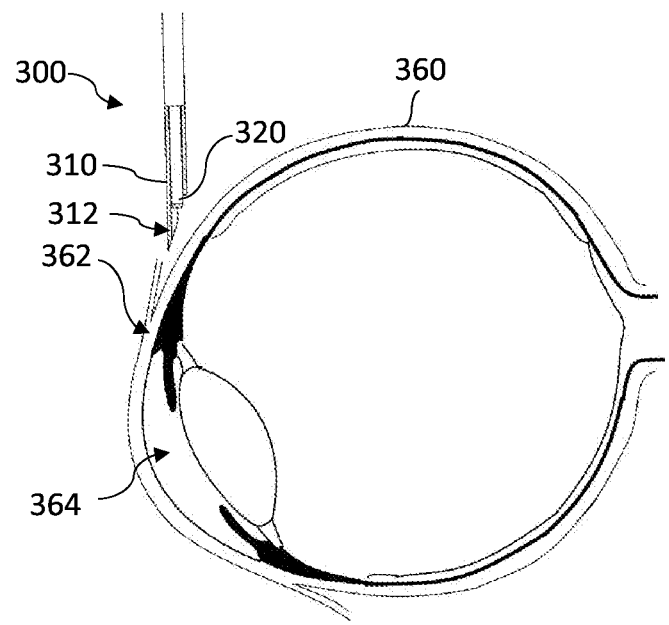
FIGS. 3A-3E exemplify a non-limiting technique for creating a channel in soft tissue according to the invention.

As shown in FIG. 3A, the device 300 approaches the eye from outside where it encounters the outer tissue layer that includes the conjunctiva and/or tenon tissues (366 in FIG. 3B) by the outer member 310, and precisely by the first distal part 312 of the outer member 310. The outer member 310 pierces and penetrates the conjunctiva and/or tenon when it is advanced forwardly, typically manually, by the surgeon.

Figure 3B:
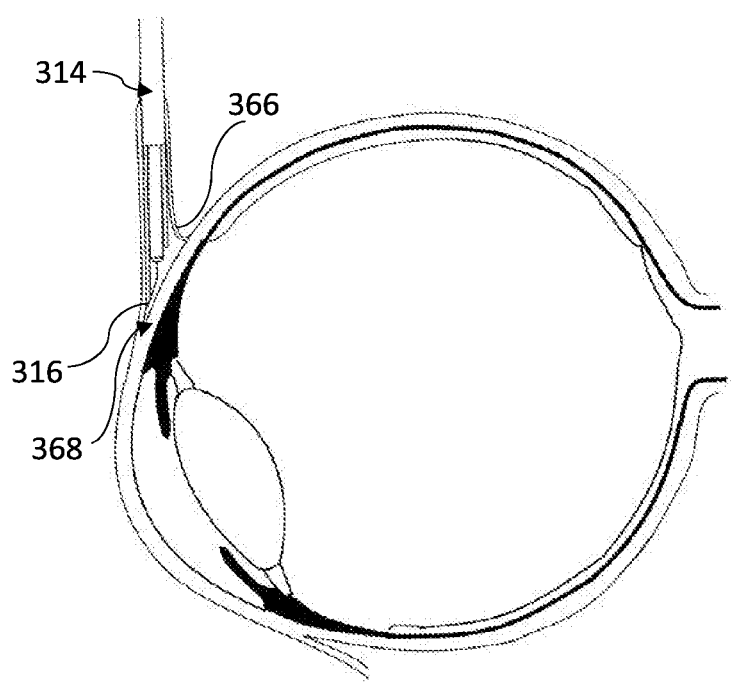

As shown in FIG. 3B, after or while the device passes the conjunctiva and tenon 366, the surgeon can pull the conjunctiva 366, and possibly also the tenon, outwardly by the help of a suitable tool held in his other hand. The conjunctiva tissue, and possibly also the tenon, now wraps the outer member 310 at the first proximal elongated part 314. This saves the conjunctiva and/or tenon by preventing them from coming into contact with the inner member which will be rotated and advanced to cut and remove sclera tissue. The tissue piercing tip 316 of the outer member 310 now contacts the sclera tissue 368.

Figure 3C:
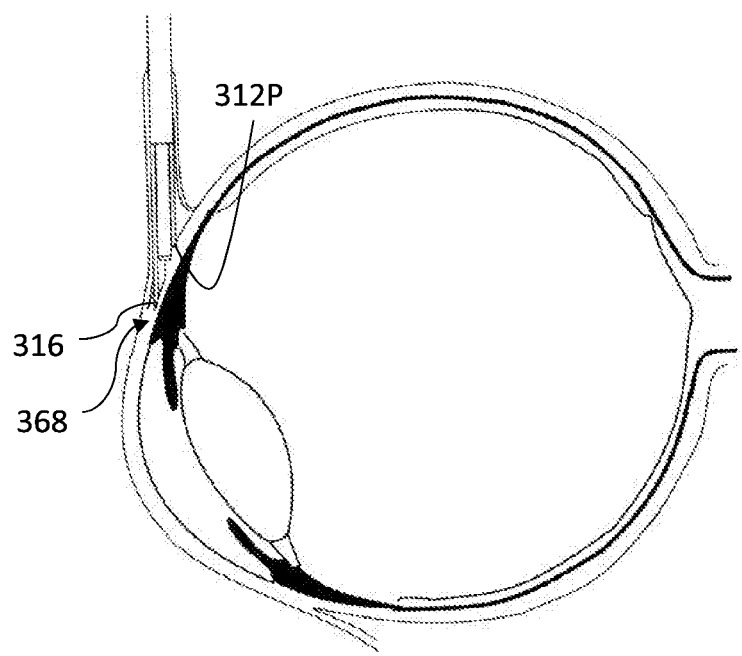

As shown in FIG. 3C, the outer member 310 is further advanced forwardly, manually, as described above, such that the piercing tip 316 penetrates the sclera tissue 368. The device, by the first distal part 312 of its outer member 310, is stuck in (anchored) and stabilized temporarily in the sclera tissue 368. During advancement inside the sclera tissue 368, the resistance-to-progression increases and is given as a feedback to the surgeon when he/she manually advances the device. In the case the device is configured with the stopper 312P, as shown in this specific example, the device 300 comes to a hard stop because the stopper 312P provides significant increase in resistance-to-progression force on the outer member 310 and prevents the additional penetration/progression inside the sclera tissue 368.

It is appreciated that FIGS. 3A to 3C illustrate the positioning phase of the device 300 as a preparation for the channeling phase. It is also appreciated, that during the positioning phase, no relative motion between the outer and inner member occurs. Generally, the inner member is hidden inside and fixedly attached to the outer member during the axial movement of the outer member, no matter how the axial movement of the outer member is executed, whether the axial movement includes manual displacement of the outer member by the surgeon relative to the handle, or whether the outer member is fixedly attached to the handle such that the axial movement of the outer member is generated by manual axial movement of the handle by the surgeon.

Figure 3D:
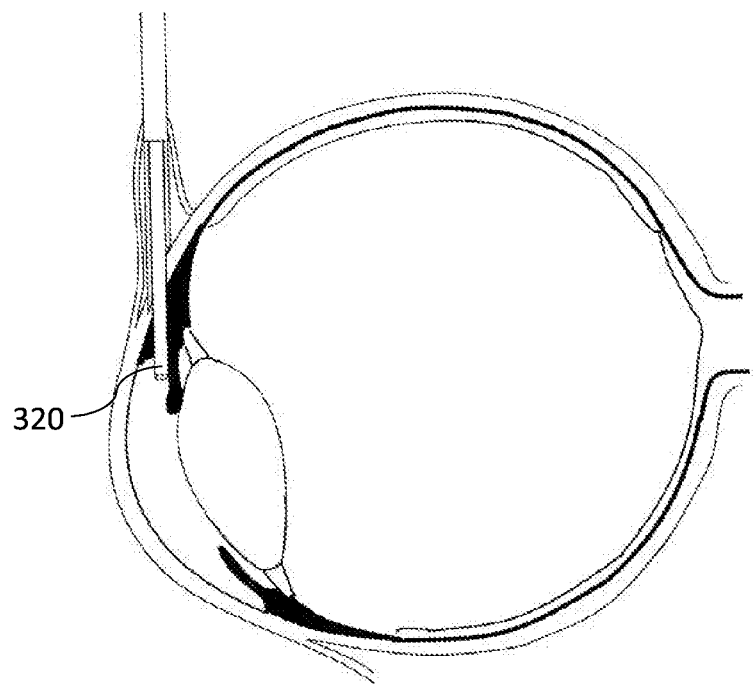

At this point, as shown in FIG. 3D and while the outer member 310 protects the conjunctiva tissue, the inner member 320 is rotated, either mechanically or electrically by a dedicated motor as described above and will be further exemplified below, and is advanced by the applied moving mechanism forwardly such that it contacts and attaches to the sclera tissue 368 and starts with drilling and creating the channel. The advancement distance of the rotating inner member can be configured by the moving mechanism such that the distal end of the inner member 320 does not protrude significantly into the anterior chamber of the eye to avoid causing harm to the internal side of the eye. The inner member 320 is then retracted backwardly (not shown), either rotating or not depending on its configuration, as will be described further below, until it is back in its secured position inside the outer member 310, and the latter is pulled out from the sclera and conjunctiva tissues by the surgeon. The conjunctival tissue recovers almost immediately and the hole therein, formed by the outer member only, closes. Moreover, as during the positioning phase the surgeon pulls the conjunctiva outwardly, then after releasing the conjunctiva the hole in the conjunctiva will be displaced with respect to the channel in the sclera. As the conjunctiva attaches back to the sclera, the risk of eye collapse due to excessive fluid exiting the eye is prevented.

Figure 3E:
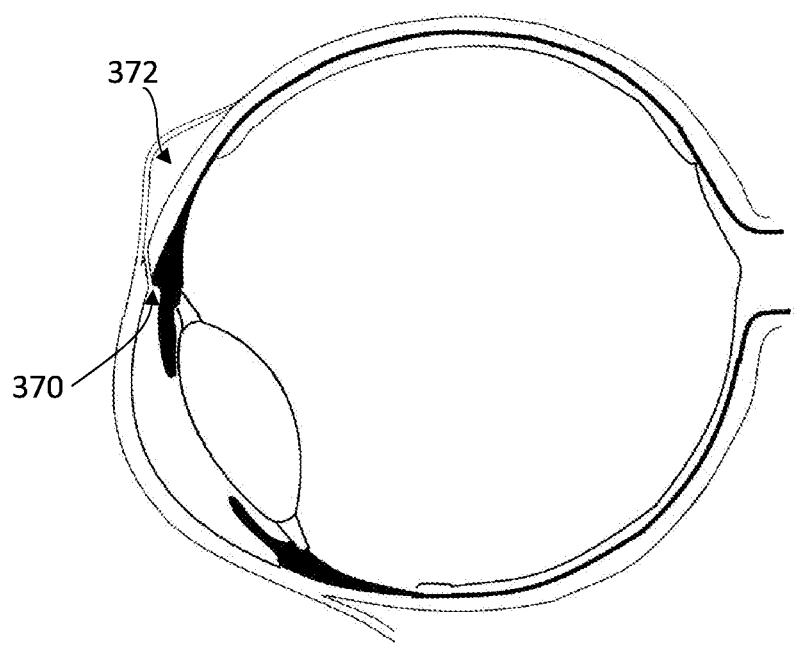

FIG. 3E illustrates the created channel 370 after the device is pulled outside the eye. The aqueous humor (the fluid in the anterior chamber) starts to exit the anterior chamber towards the sub-conjunctival space, such that a bleb 372 is formed under the conjunctiva and above the sclera, and the fluid is reabsorbed in the blood vessels at the vicinity thereof.

Figure 3F:
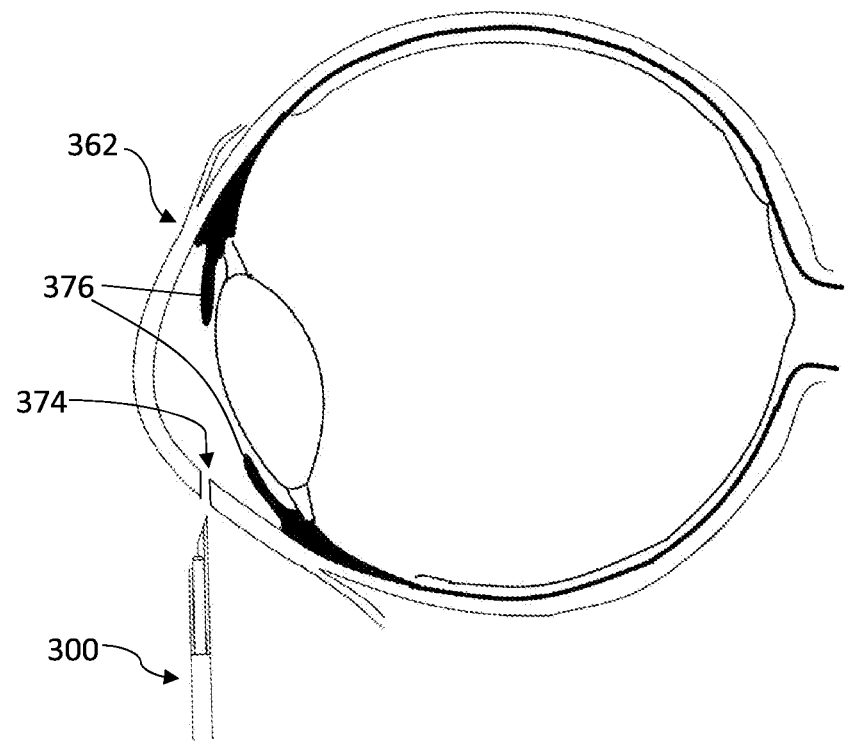
FIGS. 3F-3I exemplify another non-limiting technique for creating a channel in soft tissue according to the invention.

Reference is now made to FIGS. 3F to 3I exemplifying another non-limiting technique for creating a channel in soft tissue by using the medical device of the invention. The described example relates to creating a channel in the sclera tissue of the eye in Ab interno procedure by approaching the sclera tissue from inside of the eye. As has been mentioned above, the device of the invention is advantageous in that it can be used in either Ab externo or Ab interno procedures. For simplicity of presentation, every feature which is not referenced in the figures is assumed to be the same as in FIGS. 3A to 3E. The human eye is shown, where a channel should be created at the region of the sclera-corneal junction 362, as depicted in FIG. 3F. As described above, the created channel will controllably connect between the anterior chamber of the eye and the sub conjunctival space/zone and hence allow the extra fluid accumulated in the anterior chamber to exit and by this reduce the intraocular pressure. The properties of the channel, including its size and geometry, can be as has been described earlier with reference to FIGS. 3A to 3E. As shown in FIG. 3F, the device 300 approaches the eye from outside and is to be inserted into the anterior chamber 364 of the eye through an opening 374 created beforehand in clear cornea at the opposite side to where the channel is to be created. The opening 374 can be achieved by conventional means known in the art such as a stylet blade. The device is inserted with respect to the eye in an orientation which is opposite to the orientation described in FIGS. 3A to 3E relating to the Ab externo procedure. In other words, the tissue sharp tip of the outer member is now closer to the internal side of the eye, whereas it was farther away in the Ab externo procedure (as shown in FIG. 3A). By this, the first distal portion beveled shape and orientation will complement the shape and orientation of the sclera at the contact region 362.

The device is inserted into the anterior chamber and is pushed manually by the surgeon, while passing above the iris 376, until it contacts the sclera tissue at the sclera-corneal junction 362 from inside.

Figure 3G:
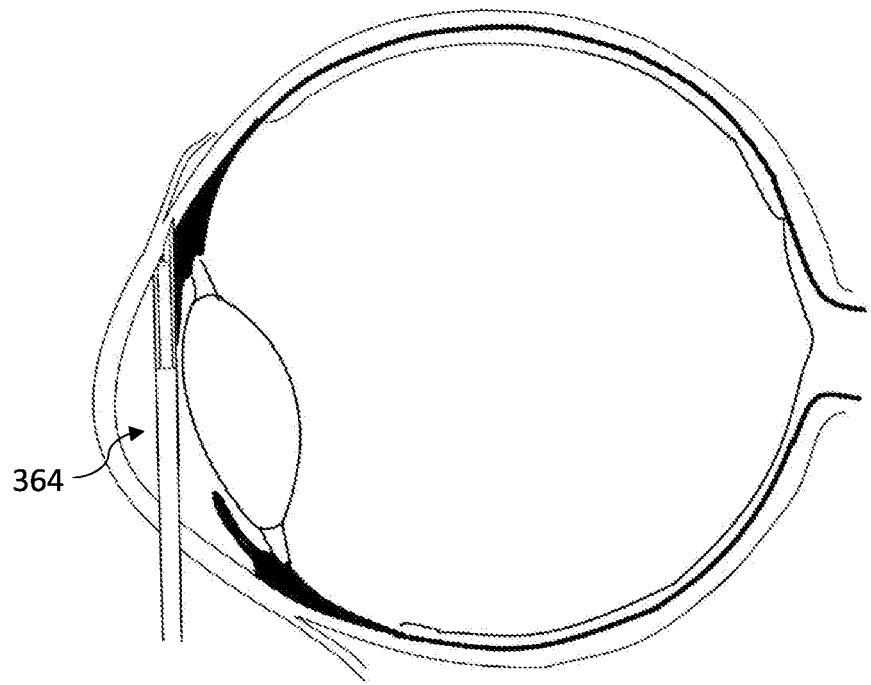

As appreciated from FIG. 3G, after the surgeon feels the contact, another pushing force is applied manually in the forward direction, such that the outer member 310 pierces and penetrates the sclera (from the inside). The device, by the first distal part 312 of its outer member 310, is stuck in (anchored) and stabilized temporarily in the sclera tissue. As described above, during advancement inside the sclera tissue, the resistance-to-progression increases and is given as a feedback to the surgeon when he/she manually advances the device. In the case the device is configured with the stopper 312P, as shown in this specific example, the device comes to a hard stop because the stopper provides significant increase in resistance-to-progression force on the outer member and prevents the additional penetration/progression inside the sclera tissue. As also described above, the pre-configured length of the first distal portion of the outer member insures that the piercing tip does not exit the sclera from the other (here external) side, such that the conjunctiva or other covering tissue is not torn or pierced by the outer member.

It is appreciated that FIGS. 3F and 3G illustrate the positioning phase of the device 300 as a preparation for the channeling phase. It is also appreciated, that during the positioning phase, no relative motion between the outer and inner member occurs. Generally, the inner member is hidden inside and fixedly attached to the outer member during the axial movement of the outer member, no matter how the axial movement of the outer member is executed, whether the axial movement includes manual displacement of the outer member by the surgeon relative to the handle, or whether the outer member is fixedly attached to the handle such that the axial movement of the outer member is generated by manual axial movement of the handle by the surgeon.

Figure 3H:
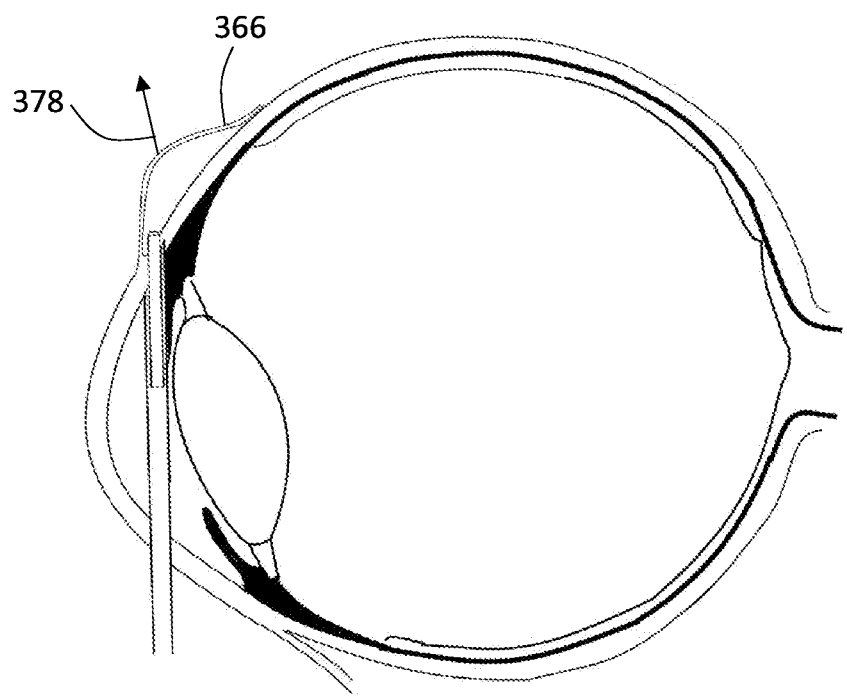

As shown in FIG. 3H, while or after the outer member is anchored into the sclera tissue, the surgeon can pull and lift the conjunctiva 366, and possibly also the tenon, outwardly in a direction 378 by the help of a suitable tool held in his other hand. This saves the conjunctiva and/or tenon by preventing them from coming into contact with the inner member which will be rotated and advanced to cut and remove sclera tissue. The inner member is rotated, either mechanically or electrically by a dedicated motor as described above and is advanced by the applied moving mechanism forwardly such that it contacts and attaches to the sclera tissue and starts with drilling and creating the channel. The advancement distance of the rotating inner member can be configured by the moving mechanism such that the distal end of the inner member does not protrude significantly outside the sclera tissue to avoid causing harm to the conjunctiva and/or tenon tissues. While the inner member rotates to cut and remove tissue from the sclera, the outer member, which is stabilized by its anchor to the sclera tissue, is stationary, it does not or hardly moves, thus preserving the internal organs, such as the iris, from any damage that may have been caused by the rotating inner member. Further, its anchoring to the sclera minimizes any accidental pulling of the rotating inner member from the sclera, something which may otherwise have adverse consequences on the internal organs of the eye. After creating the channel, the inner member is retracted backwardly (not shown), either rotating or not depending on its configuration, as will be described further below, until it is back in its secured position inside the outer member, and the device is pulled backwardly out from the anterior chamber and out of the eye through the opening 374 which can be treated by suitable medicines in order to heal and close almost immediately.

Figure 3I:
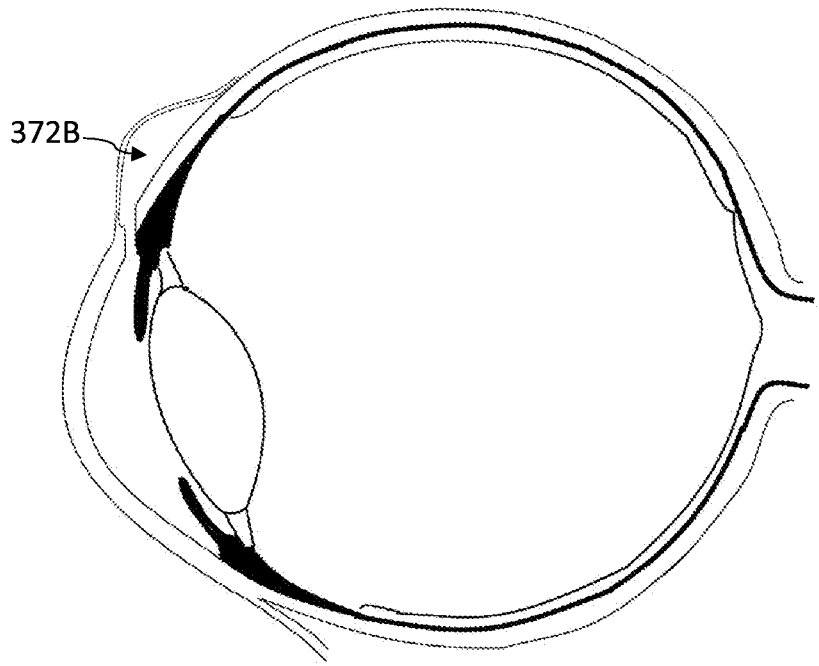

FIG. 3I illustrates the created channel after the device is pulled outside the eye. The aqueous humor (the fluid in the anterior chamber) starts to exit the anterior chamber towards the sub-conjunctival space, such that a bleb 372B is formed under the conjunctiva and above the sclera, and the fluid is reabsorbed in the blood vessels at the vicinity thereof.

Reference is made to FIGS. 4A to 4D showing various non-limiting examples of the outer member of the device according to some non-limiting embodiments of the invention. The figures are illustrative only and are not presented in a full scale. Specifically, the figures show different non-limiting configurations of the first distal portion of the outer member. Generally, the shape and/or orientation of the first distal part can be chosen to complement the shape and/or orientation of the target tissue, such that better coupling/attachment/adherence/anchoring between the outer member and the target tissue is achieved.

FIG. 4A shows a known shape of cannula end used in medical needles. This is a common point cannula end known as flat bevel point. This configuration can be used as the first distal part 412A of the outer member 410A.

FIG. 4B also shows a known shape of cannula end used in medical needles. This is a common point cannula end known as lancet bevel point. This configuration can be used as the first distal part 412B of the outer member 410B.

FIG. 4C shows a special non-limiting example of a first distal part 412C of an outer member 410C according to the invention. Similar configuration to FIG. 4C is also shown in FIGS. 2A and 2B. The first distal part 412C includes a tissue piercing tip 416C configured as a lancet bevel point and a stopping portion 412PC formed by the rim of the outer member 410C which is obtained by cutting a section of the wall of the outer member 410C along its longitudinal axis. In some exemplary, non-limiting, embodiments, half of the wall (e.g. half of cylinder) is cut.

FIG. 4D shows another special non-limiting example of a first distal part 412D of an outer member 410D according to the invention. The first distal part 412D includes a tissue piercing tip 416D and a stopping portion 412PD both obtained by cutting the outer member 410D in the direction of the longitudinal axis along a curved line. The curved line can be chosen to provide smooth transition along the first distal part enabling smooth penetration with increasing resistance-to progression force. The curved line is usually configured as a smooth, continuous line with constant or variable slope (its derivative trend is always positive or always negative, though not necessarily constant), although other non-continuous behavior can be used. For example, the curved line can be a combination of two or more line segments, among which some are curved and/or straight. Specifically, the piercing portion can be configured as a curved line while the stopping portion can be configured as a straight line, e.g. in the direction of the transverse cross section of the inner member. In some embodiments, such a smooth curved line can follow a circular, elliptical, semi-circular or semi-elliptical path, e.g. can be part of a circle's or an ellipse's circumference. In the example shown, an elliptical curve is presented, such that the elliptical major axis lies in the direction of the longitudinal axis of the outer member and the elliptical minor axis is in the orthogonal direction (across the outer member). In this instance, the major axis defines the length of the first distal part, and the minor axis (or, more specifically the relation between major and minor axes) defines the level of resistance-to-progression of the stopping portion 412PD. It should be understood, that the above-described example relates to formation of a curved line, forming the piercing tip/stopper, along the longitudinal axis direction, from a single direction (2D forming), while any other shaping combination in 3D is also possible.

As has been clarified above, any configuration of the outer member can be used with any configuration of the inner member. Also, it should be noted that all the examples presented here are by no means limiting and the invention can be practiced with other specific suitable configurations.

The inner member is configured, as described above, for attaching effectively to the second tissue (in which the channel is formed) and for cutting a well-defined geometrical shape of the tissue, both while rotating and advancing distally. In some embodiments, the inner member is configured for storing the cut tissue in its intact form, thus providing a validation and authentication to the created channel. In addition, storing the cut tissue inside the inner member (in the second proximal elongated part) serves in protecting the eye from sudden collapse by blocking the outflow of aqueous humor from the anterior chamber during the channel creation and/or when the device is pulled outwardly from the eye.

Reference is made to FIGS. 5A-5D showing non-limiting examples of the inner member of the device according to some non-limiting exemplary embodiments of the invention. The different examples can be distinguished by the specific channel creating application, including the specific dimensions of the channel which is affected by its purpose and its location in the body. Specifically, some of the described examples may be more suitable than others for the application of creating a channel in the eye wall for treating elevated IOP.

Figure 5A:
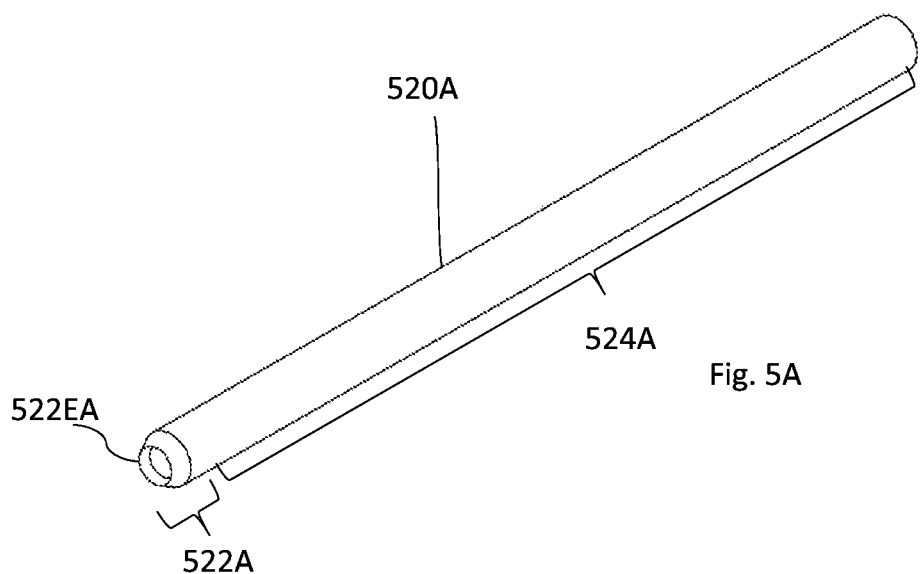

FIG. 5A illustrates an inner member 520A having a second distal part 522A configured to attach to tissue and cut tissue, while rotating and progressing distally, and to guide the inner member through the tissue, e.g. towards the anterior chamber of the eye. The inner member also includes a second proximal elongated part 524A that includes an elongated chamber/cavity (not shown) configured to receive therein the tissue being removed. The outer diameter of the inner member should preferably match the inner diameter of the outer member such that no space is left there between. The shape of the chamber/cavity preferably matches the shape of the cut tissue. In action, the inner member approaches the tissue while rotating (at least the second distal part), so that the rotation creates desired attachment of the inner member to the tissue and enables start of the piercing and cutting. Generally, the second distal part 522A has at the distal end a round cutting edge 522EA, typically of a circular shape, having one of the following configurations:

the round cutting edge 522EA has a diameter equal to the diameter of the elongated cavity, such that the cutting edge is created by sharpening (grinding) in the direction from the outer diameter of the inner member towards the diameter of the elongated cavity;

the round cutting edge 522EA has a diameter equal to the outer diameter of the inner member, such that the cutting edge is created by sharpening in the direction from the diameter of the elongated cavity towards the outer diameter of the inner member; and the round cutting edge 522EA has a diameter bigger than the diameter of the elongated cavity and smaller than the outer diameter of the inner member, such that the cutting edge is created by sharpening in both directions, from the outer diameter of the inner member towards the diameter of the elongated cavity and from the diameter of the elongated cavity towards the outer diameter of the inner member.

It was found by the inventors that the degree of sharpening, i.e. the inclination angle, plays an important role in providing effectively desired piercing of and/or attachment to the tissue.

Figure 5B:
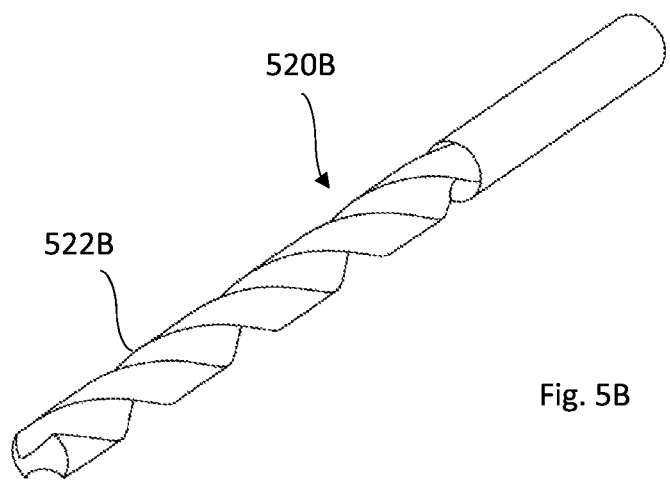

FIG. 5B illustrates another non-limiting example of the inner member 520B. In this example, the inner member is configured as a full-bodied, not hollow, elongated member with a second distal part 522B configured as a drill bit being provided with a flute enabling creating the desired channel in soft tissue while rotating. The length, spiral, point angle and lip angle of the drill bit can all be adjusted for optimal soft tissue removal. In this instance, the inner member 522B rotates with full rounds clockwise or anticlockwise, depending on the spiral direction, such that the removed tissue is conveyed backwardly far from the target tissue and towards a collecting cavity located between the inner member and the outer member of the device.

FIGS. 5C1-5C3 illustrate another non-limiting example of the inner member 520C. FIG. 5C1 is an isometric view of the inner member 520C. FIG. 5C2 is an isometric view of the coaxial outer and members, 510C and 520C, with half of the wall of the outer member at the distal side removed for easy illustration. FIG. 5C3 illustrates a transverse cross section of the outer and inner members made along the line C-C in FIG. 5C2. In this example, the inner member is configured partially similar to the example of FIG. 5A in that, as shown, the inner member 520C has a second distal part 522C configured to attach to tissue and cut tissue by its cutting edge 522EC, while rotating and progressing distally, and to guide the inner member through the tissue. The inner member 520C also includes a second proximal elongated part 524C that includes an elongated chamber/cavity 526C (inside the second proximal elongated part 524C, shown in FIG. 5C3) configured to receive therein the tissue being removed. As also shown, the second proximal elongated part 524C of the inner member 520C includes a tissue trapper 524TC at a distal segment 524DC of the second proximal elongated part 524C, located substantially in parallel to the elongated cavity 526C. The tissue trapper/tissue-trapping enhancer 524TC enhances and contributes to the trapping of the removed tissue during its removal, such that it allows/ensures pulling the removed tissue out of the body. In addition, the tissue trapper 524TC can facilitate the flow of the removed tissue into the cavity 526C by minimizing issues of clogging. In some embodiments, additionally or alternatively, the cavity in the inner member of the device can be designed to trap or contribute to trapping of the tissue there inside. In this example, the tissue trapper 524TC includes a slit 524SC, located in the longitudinal direction, i.e. along at least part of the cavity 526C. The slit 524SC is obtained by tangential cutting of the round wall of the inner member along the distal segment 524DC, i.e. by cutting in the tangential direction to the inner member's wall/circumference. It should be noted that generally the tissue trapper 524TC can include more than one slit along the inner member circumference, each slit being formed by tangential cutting along the longitudinal axis. FIG. 5C2 illustrates the device either during the positioning phase or after the device has been pulled out of the body, while in both cases the inner member (and the removed tissue in the after operation case) is located safely inside the outer member. As shown in FIGS. 5C2 and 5C3 the tangential cutting of the inner member's wall forms, in addition to the slit 524SC, a depression 524D along the distal segment 524DC of the inner member. The depression 524D causes the formation of a second outer cavity 528C between the inner and outer members, that may enhance the pulling of the removed tissue towards the cavity 526C and/or the inside of the outer member 510C. In other words, the depression 524D, resulting from the tangential cutting, forms part of the tissue trapper 524TC.

FIGS. 5D1-5D3 illustrate another non-limiting example of the inner member 520D including a tissue trapper/tissue-trapping enhancer 524TD. FIG. 5D1 is an isometric view of the inner member 520D. FIG. 5D2 is an isometric view of the coaxial outer and members, 510D and 520D, with half of the wall of the outer member in the distal side removed for easy illustration. FIG. 5D3 illustrates a transverse cross section of the outer and inner members made along the line D-D in FIG. 5D2. As can be appreciated, various features and elements in FIGS. 5D1-5D3 are similar to those in FIGS. 5C1-5C3. Specifically, as shown in FIG. 5D1, the inner member 520D has a second distal part 522D configured to attach to tissue and cut tissue by its cutting edge 522ED, while rotating and progressing distally, and to guide the inner member through the tissue. The inner member 520D also includes a second proximal elongated part 524D that includes an elongated chamber/cavity 526D (inside the second proximal elongated part 524D, as shown in FIG. 5D3) configured to receive therein the tissue being removed. The second proximal elongated part 524D of the inner member 520D includes a tissue trapper 524TD at a distal segment 524DD of the second proximal elongated part 524D, located substantially in parallel to the elongated cavity 526D. As has been explained, the tissue trapper 524TD enhances and contributes to the trapping of the removed tissue during its removal, such that it allows/ensures pulling the removed tissue out of the body. In addition, the tissue trapper 524TD can facilitate the flow of the removed tissue into the cavity 526D by minimizing issues of clogging. In some embodiments, additionally or alternatively, the cavity in the inner member of the device can be designed to trap or contribute to trapping of the tissue there inside. In this example, the tissue trapper 524TD includes a slit 524SD, located in the longitudinal direction, i.e. along at least part of the cavity 526D. The slit 524SD is obtained by radial cutting of the round wall of the inner member along the distal segment 524DD, i.e. by cutting in the radial direction of the inner member. It should be noted that generally the tissue trapper 524TD can include more than one slit along the inner member's circumference, each slit being formed by radial cutting in the radial direction and along the longitudinal axis. FIG. 5D2 illustrates the device either during the positioning phase or after the device has been pulled out of the body, while in both cases the inner member (and the removed tissue in the after operation case) is located safely inside the outer member.

Turning now to FIGS. 5E1 to 5E7 illustrating one non-limiting scenario of removing soft tissue from a tissue layer in the body. Specifically, the figures illustrate undesired effect of tearing of the soft tissue, instead of or in addition to cutting, while rotating the cutting tool inside the tissue.

Ideally, the channel created in the tissue can be expected to look as shown in FIG. 5E1, i.e. it should have a cylindrical shape, such as when the inner member is as described in FIG. 5A. The channel 5003 connects between outer scleral surface 5002 and inner scleral surface 5001. The cutting tool 520E, e.g. the inner member, rotates in a direction 503E around its longitudinal axis, either clockwise or anticlockwise or reciprocating in both directions, and approaches the sclera under feeding rate 502E. In preferable scenario, the channel should have the required dimensions while its diameter is similar to the diameter of the cutting edge 522EE. The removed tissue 5004 is expected to be trapped within the cutting tool 520E as shown in FIG. 5E2.

It is appreciated that cutting of the tissue is defined by the tissue behavior and characteristics. As the cutting tool 520E cuts, it rotates/revolves within the tissue. The treated organ (e.g. —the eye) is static while the cutting tool 520E rotates/turns. The cutting tool 520E presses the tissue both by its external surface 504E (outer diameter) and inner diameter 505E. The diameter of the cylindrical tissue 5004 is defined by the cutting edge 522EE yet the inner diameter 505E might be slightly smaller and causes squeezing of the tissue (within the cavity of the cutting tool). Another reason for squeezing of the tissue inside the cavity of the cutting tool can be a relatively high friction force between the tissue and the inner surface of the cavity. Additional reason for squeezing of the tissue inside the cavity might be the limited length of the cavity as shown in FIG. 5E3 which is a magnified image of a cutting tool, captured by a microscope. The current technology enables creating a cavity with a small diameter, as required in the treatment of the eye, with length up to about 0.5 mm, as illustrated by the step 508E in the figure. However, the required length for the channel may be longer than that, for example it should be about three times more (1.5 mm) when the channel is to be created in the sclera in the eye wall.

Since the cutting tool 1 (e.g. the inner member) rotates and the tissue (e.g., the eye) is static, the tissue 5004 is expected to remain static until the cutting process is completed. In reality, during the cutting process, as shown in FIGS. 5E4 and 5E5, the tissue 5004 is defined by two sections, tissue section 5041 pressed into the cavity of the cutting tool and tissue section 5042 still un-pressed. The attachment of tissue section 5041 to the inner surface of the cavity, due to high friction or due to insufficient cavity length, may cause tissue section 5041 to start rotating with the cutting tool and to tear apart from tissue section 5042. In this case, the separation of tissue 5004 is not caused by cutting, but rather by torsional tearing. Accordingly, the channel created within the eye wall might look as shown in FIG. 5E6 or 5E7. This may result in insufficient and ineffective drainage, or even no drainage at all.

Minimizing the radial attachment of the removed tissue to the inner surface of the cavity in the cutting tool enables continuation of cutting rather than tearing. Reducing the radial attachment force between the removed tissue (e.g., tissue 5041) and inner surface of the cavity (e.g., surface 505E) can be achieved by lowering the friction coefficient between the tissue and the inner surface of the cavity (for example by applying low friction coating on the inner surface). Alternatively or additionally, Reducing the radial attachment between the removed tissue and inner surface of the cavity can be achieved by creating specific geometry of the cutting tool, e.g. by making the diameter of the inner surface of the cavity bigger than the diameter of the cutting edge of the cutting tool.

Turning now to FIGS. 5F-5G showing non-limiting exemplary embodiments of tissue cutting tools and methods of fabrication and/or optimization. The cutting tools are optimized for cutting soft tissue and for creating a channel with predetermined dimensions and geometry in a specific given tissue while minimizing the effect of tearing. In some embodiments, the inner member of the device of the invention can be configured as the cutting tools described in FIGS. 5F and 5G. Therefore, the reference numbers used in the following figures follow the same numbering used so far, for example 520E denotes a tissue cutting tool that can be used as the inner member of the device of the invention. However, this should not be interpreted as limiting the invention.

FIG. 5F shows a first non-limiting example of a cutting tool configured according to some embodiments of the present invention. The figure describes a cutting tool 520E which can minimize the radial attachment between the removed tissue and the cavity's inner surface to thereby minimize the effect of tearing of the tissue. This can be achieved by shaping of the cutting tool. As shown in the figure, a distal portion 504F of the cutting tool is shaped and pressed towards rotation axis of the tool (passing at the center of the tool if the tool is symmetrical and isotropic). Pressing and shaping can be made by means of known techniques, such as swaging and spinning. In this case, the diameter of the cutting edge 522EF at the distal end of the cutting tool is smaller than the inner diameter 505F of the cavity inside the cutting tool. As the diameter of the cutting edge determines the diameter of the removed tissue, the cutting tool 520F is expected to provide minimal or no attachment force on the removed tissue inside the tool and by this improve the trapping of the removed tissue, while minimizing tearing risk and preserving full shape of the removed tissue that matched a full open channel inside the tissue wall.

FIGS. 5G1 to 5G4 illustrate non-limiting exemplary cutting tools 520G1 (in FIG. 5G3) and 520G2 (in FIG. 5G4) and an exemplary process for producing the cutting tools (FIGS. 5G1 and 5G2), according to some embodiments of the invention.

In FIG. 5G1, a side view (cross section) of tool 520G includes at a distal side 501G a hollow cylinder 506G having a cavity 507G between uniform outer and inner diameters, 504G and 505G respectively, that extend along a longitudinal (rotation) axis X1. In FIG. 5G2, a close-up view on the cylinder 206G is shown. A distal portion 504G is shaped with a predetermined pattern, e.g. by pressing, such that both the inner and outer diameters decrease towards the distal end 509G of the hollow cylinder. As shown on the proximal end 511G of the hollow cylinder, the original inner and outer diameters are about 0.17 mm and 0.3 mm respectively, and the modified inner and outer diameters at the distal end 509G are about 0.13 mm and 0.27 mm respectively. The shaping of the distal portion can be done by, for example but not limited to, swaging and/or spinning techniques. The pattern of shaping can be linear, for example by tapering the distal portion to provide a substantially cylindrical frustum shape, or non-linear, e.g. by following a curved line such as parabolic or other similar pattern.

In a next step, a slice of the hollow cylinder's side wall is removed (to the right, in the figure) along the longitudinal axis, in the proximal direction, starting from the distal end 509G. Depending on the slice depth (i.e. thickness), two exemplary cutting tools 520G1 and 520G2 are shown in FIGS. 5G3 and 5G4. A cutting edge 522EG is formed at the distal end and the inner and outer diameters become almost equal, such as 0.18 mm in FIG. 5G3 and 0.16 mm in FIG. 5G4. Additional sharpening of the cutting edge, both from inside and outside directions results in that the cavity, at a distal side thereof, has a slightly smaller diameter than the cutting edge's diameter. Then, the inner diameter of the cavity increases continuously in the proximal direction (to the right in the figures) until the inner diameter of the cavity reaches the higher value 505G of the proximal side of the hollow cylinder. Alternatively, the slicing of the inner surface of the cavity may provide a substantially constant inner cavity diameter. By this slicing step, no step (such as step 508E in FIG. 5E3) is present, and the cavity will have at least a length, in the longitudinal axis direction, equal to the original hollow cylinder's cavity length, thus providing receiving cavities longer than the limit of 0.5 mm and wide enough to thereby minimize attachment of the tissue entering the cavity to the inner surface of the cavity. All at a micro level required for applications such as creating safe enough channels in the eye wall.

Other non-limiting examples of the inner member include devices as described in WO2013186779 and WO2015145444 both assigned to the assignee of the present invention.

As described above, the various movements of the outer and inner member of the device are performed either manually and/or by using a moving/movement mechanism. The outer member is configured for axial movement only, while the inner member is configured for both rotational and axial movements. Typically, the inner member's rotation is governed by an electrical motor connected to the proximal side of the inner member. This is not particularly described here, examples can be found in the above mentioned patent application PCT/IL2016/051063 assigned to the assignee of the present invention. In the following, a variety of moving/movement mechanisms are described.

Figure 6C:
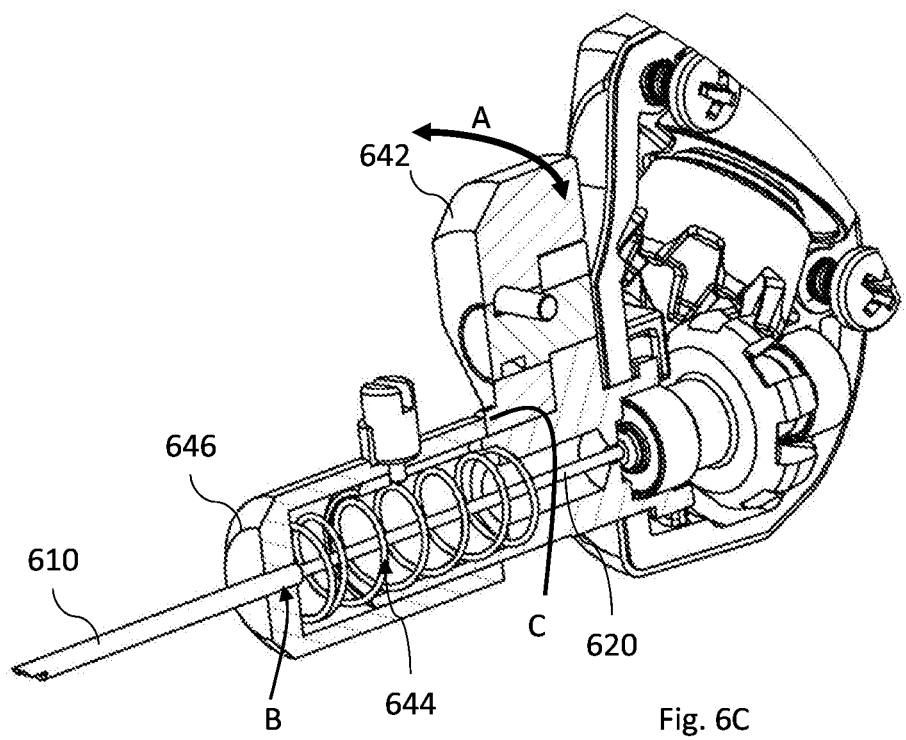
Figure 6D:
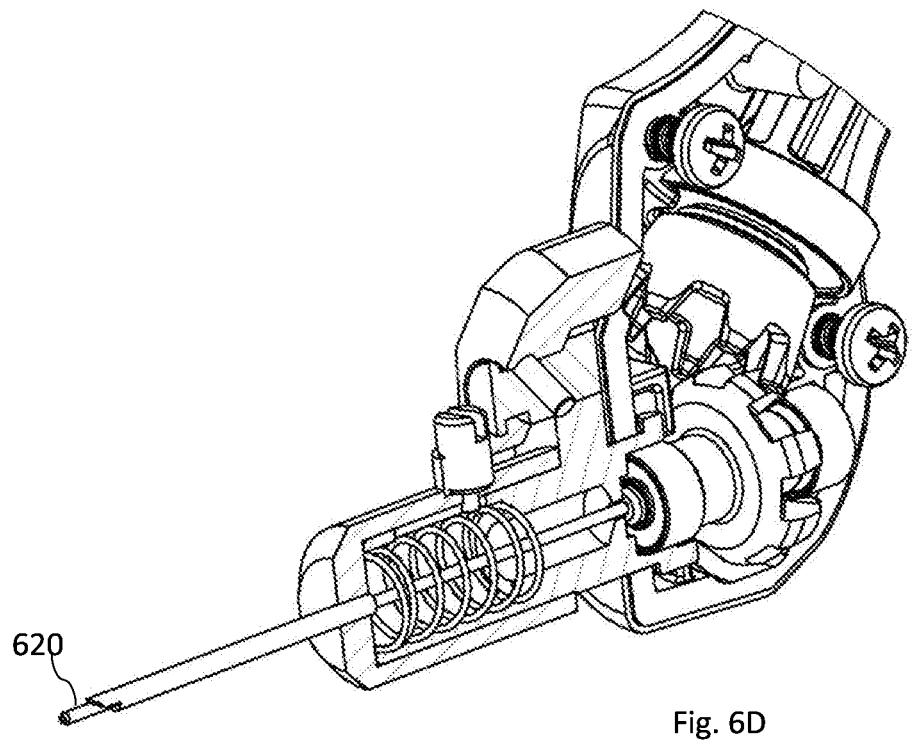

Reference is made to FIGS. 6A to 6D illustrating a non-limiting example of a movement mechanism configured for manual movement of the device during operation. As shown, the device 600 includes outer member 610 and inner member 620 mounted on a handle 650 via a movement mechanism 640. FIGS. 6A and 6C show the device during the positioning phase, i.e. when the outer member is moved forwardly (by manual pushing of the handle by the operating surgeon) to pierce first (preceding) and second (target) tissue layers, or to approach and stick into the target layer directly (such as in the Ab interno procedure). FIGS. 6B and 6D show the device during the channeling phase, i.e. when the inner member is rotated, by an electric motor (not shown), and advanced distally to cut and remove tissue, thereby leaving the channel in the target tissue layer.

The movement mechanism 640 includes a latch 642, a spring 644, and a housing 646. As shown in FIG. 6C, the latch is movable to the sides as illustrated by the arrow A. The outer member 610 is axially locked by being firmly attached to the housing at B and supported by the latch 642 at C. The spring 644 is slightly pre-compressed/relaxed during the positioning phase.

After pushing the device with the handle 650 inside the tissue until the first distal part of the outer member is stuck/anchored temporarily inside the target tissue layer, e.g. in the sclera, as described above, the operating surgeon turns the latch 642 to the left (or to the right) releasing the outer member 610 at C, thus enabling its retraction proximally. The surgeon switches the electrical motor to rotate the inner member and pushes distally with the handle 650 to expose the inner member 620 as in FIG. 6D. The outer member 610 retracts and the spring 644 is compressed. The channel creation occurs once the surgeon pushes the device distally. While the compressed spring 644 tends to push the outer member 610 distally, the spring's constant is chosen to be too low to enable further penetration of the outer member to the sclera. Ergonomically, the surgeon can control over all features using a single finger while holding the handle.

Figures 7A, 7B:
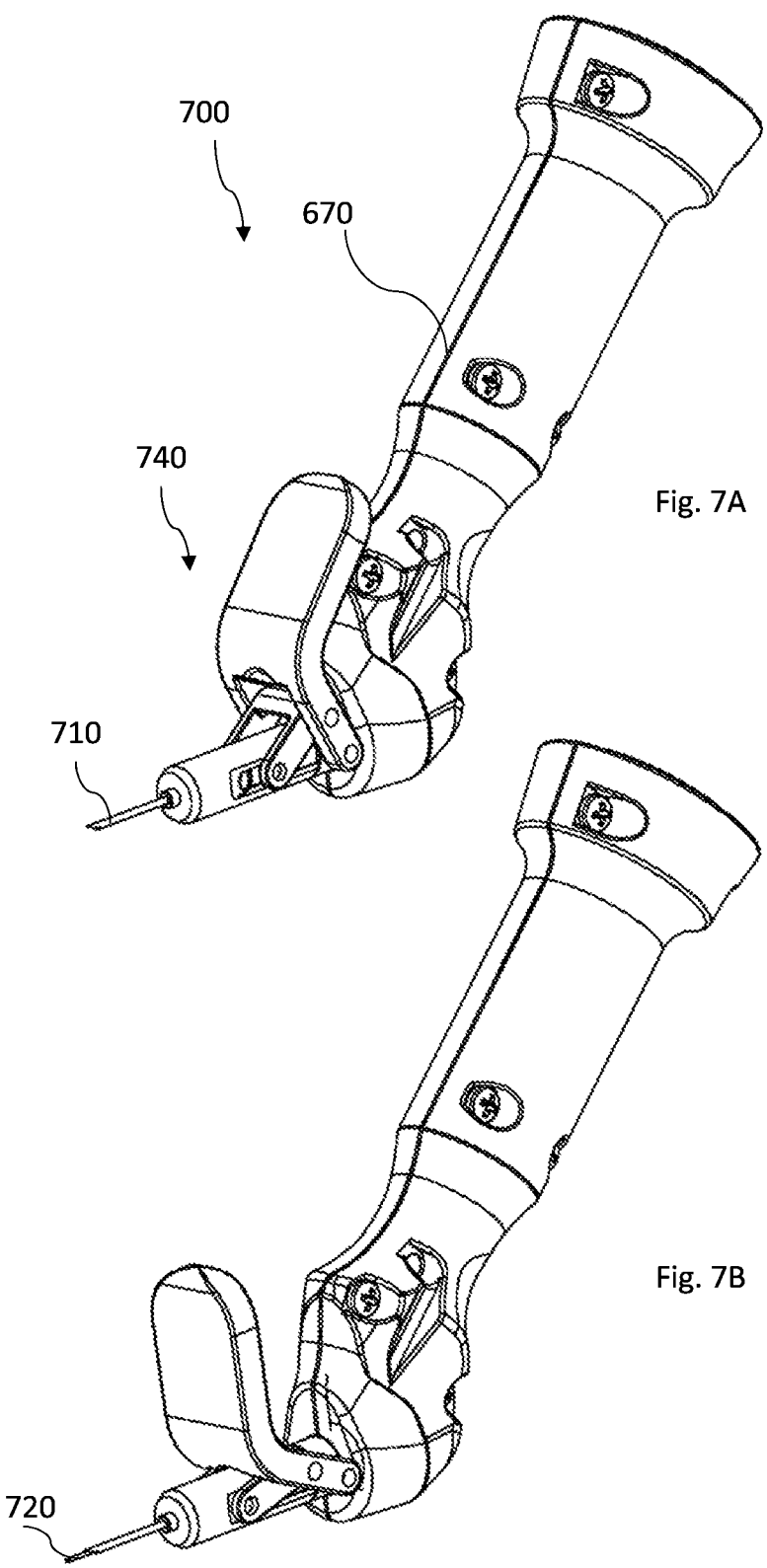
FIGS. 7A-7D illustrate another non-limiting example of manual movement mechanism according to the invention.
Figures 7C, 7D:
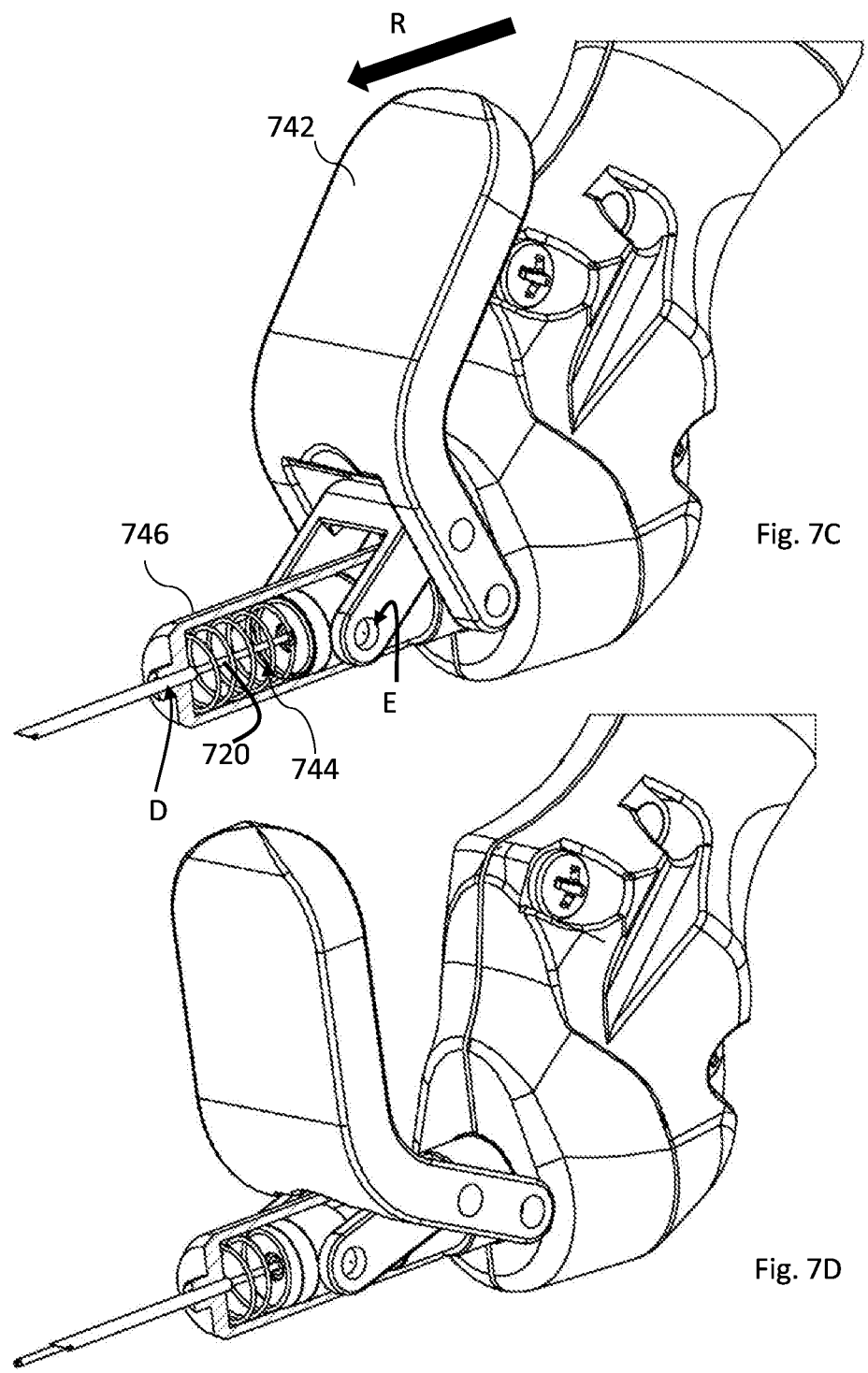

Reference is made to FIGS. 7A to 7D illustrating another non-limiting example of a movement mechanism configured for manual movement of the device, specifically the inner member, during operation. As shown, the device 700 includes outer member 710 and inner member 720 mounted on a handle 750 via a movement mechanism 740. FIGS. 7A and 7C show the device during the positioning phase, i.e. when the outer member is moved forwardly (by manual pushing of the handle by the operating surgeon) to pierce one or more tissue layers and/or until being inserted and anchored in the target tissue layer. FIGS. 7B and 7D show the device during the channeling phase, i.e. when the inner member is rotated, by an electric motor, and advanced distally to create the channel in the second tissue layer.

The movement mechanism 740 is configured for controllably advancing the inner member (distally) by manual pushing movement. As shown in FIG. 7C, the movement mechanism 740 includes a knob 742, a spring 744, and a housing 746. The outer member 710 is axially locked by being fixedly attached to the housing at D, and as a result also to the handle 750, such that when the operating surgeon pushes the handle 750 towards the tissue, the outer member moves in the axial direction and penetrates the tissue until it sticks in the sclera. The spring 744 is relaxed during the positioning phase.

The knob 742 is attached to the proximal side of the inner member 720 at E, such that they move together in the distal and proximal directions. During the channeling phase, the knob 742 is controllably pushed in the distal direction by the operating surgeon, as shown by arrow R, against the spring 744 causing it to compress. The inner member moves distally at the same rate by which the operating surgeon pushes the knob 742. Upon releasing the knob 742, a retraction movement occurs, the spring 744 relaxes and pulls the knob 742 as well as the inner member 720 proximally to the closed state as in FIG. 7C. Additionally, though not specifically illustrated, the movement mechanism may include a latch configured to lock the knob 742 in the forward position, and only when the latch is released by the operating surgeon, the retraction movement occurs. As mentioned, the rotational movement of the inner member is controlled by an electrical motor which is not specifically described herein.

Figures 8A, 8B:
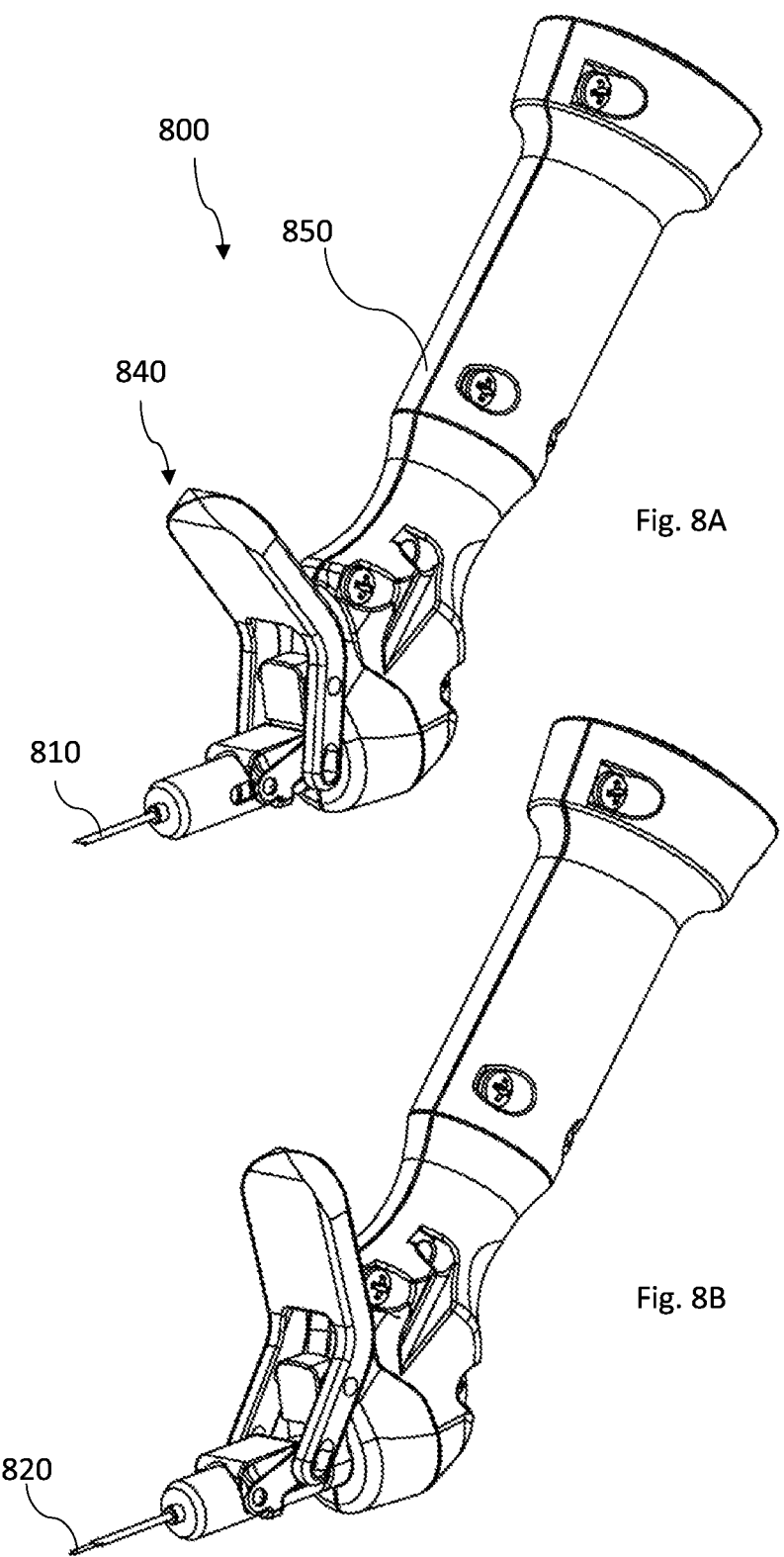
FIGS. 8A-8D illustrate yet another non-limiting example of manual movement mechanism according to the invention.
Figure 8C:
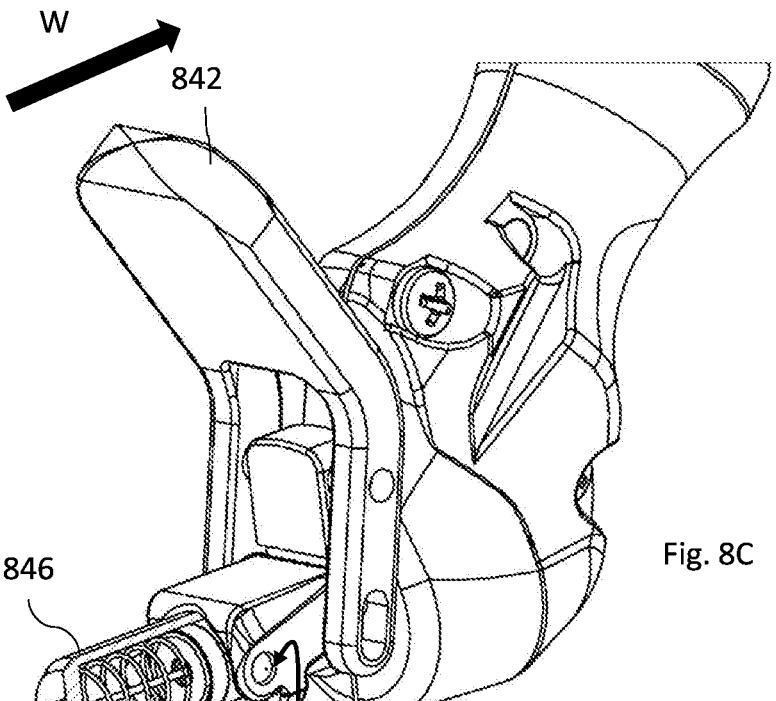
Figure 8D:
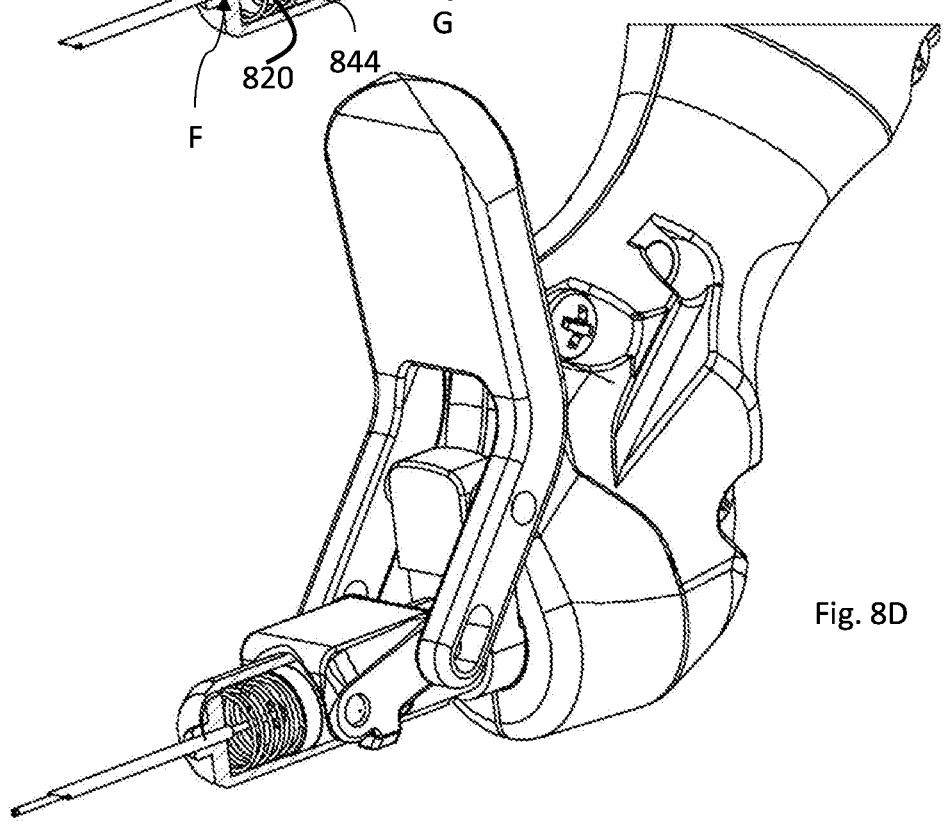

Reference is made to FIGS. 8A to 8D illustrating another non-limiting example of a movement mechanism configured for manual movement of the device, specifically the inner member, during operation. As shown, the device 800 includes outer member 810 and inner member 820 mounted on a handle 850 via a movement mechanism 840. FIGS. 8A and 8C show the device during the positioning phase, i.e. when the outer member is moved forwardly (by manual pushing of the handle by the operating surgeon) to pierce one or more tissue layers and/or until being inserted and anchored in the target tissue layer. FIGS. 8B and 8D show the device during the channeling phase, i.e. when the inner member is rotated, by an electric motor (not shown), and advanced distally to create the channel in the target tissue layer.

The movement mechanism 840 is configured for controllably advancing the inner member (distally) by manual pulling movement. As shown in FIG. 8C, the movement mechanism 840 includes a knob 842, a spring 844, and a housing 846. The outer member 810 is axially locked by being fixedly attached to the housing at F, and as a result also to the handle 850, such that when the operating surgeon pushes the handle 850 towards the tissue, the outer member moves in the axial direction and penetrates the tissue until it sticks in the sclera. The spring 844 is relaxed during the positioning phase.

The knob 842 is attached to the proximal side of the inner member 820 at G, such that they move together in the distal and proximal directions. During the channeling phase, the knob 842 is controllably pulled in the proximal direction by the operating surgeon, as shown by arrow W, such that G moves distally against the spring 844 causing it to compress. The inner member moves distally at the same rate by which the operating surgeon pulls the knob 842. Upon releasing the knob 842, it moves in the distal direction, the spring 844 relaxes and pushes G as well as the inner member 820 proximally to the closed state as in FIG. 8C. Additionally, though not specifically illustrated, the movement mechanism may include a latch configured to lock the knob 842 in the backward position, and only when the latch is released by the operating surgeon, the retraction movement of the inner member occurs. As mentioned, the rotational movement of the inner member is controlled by an electrical motor which is not specifically described herein.

Figures 9C, 9D, 9E:
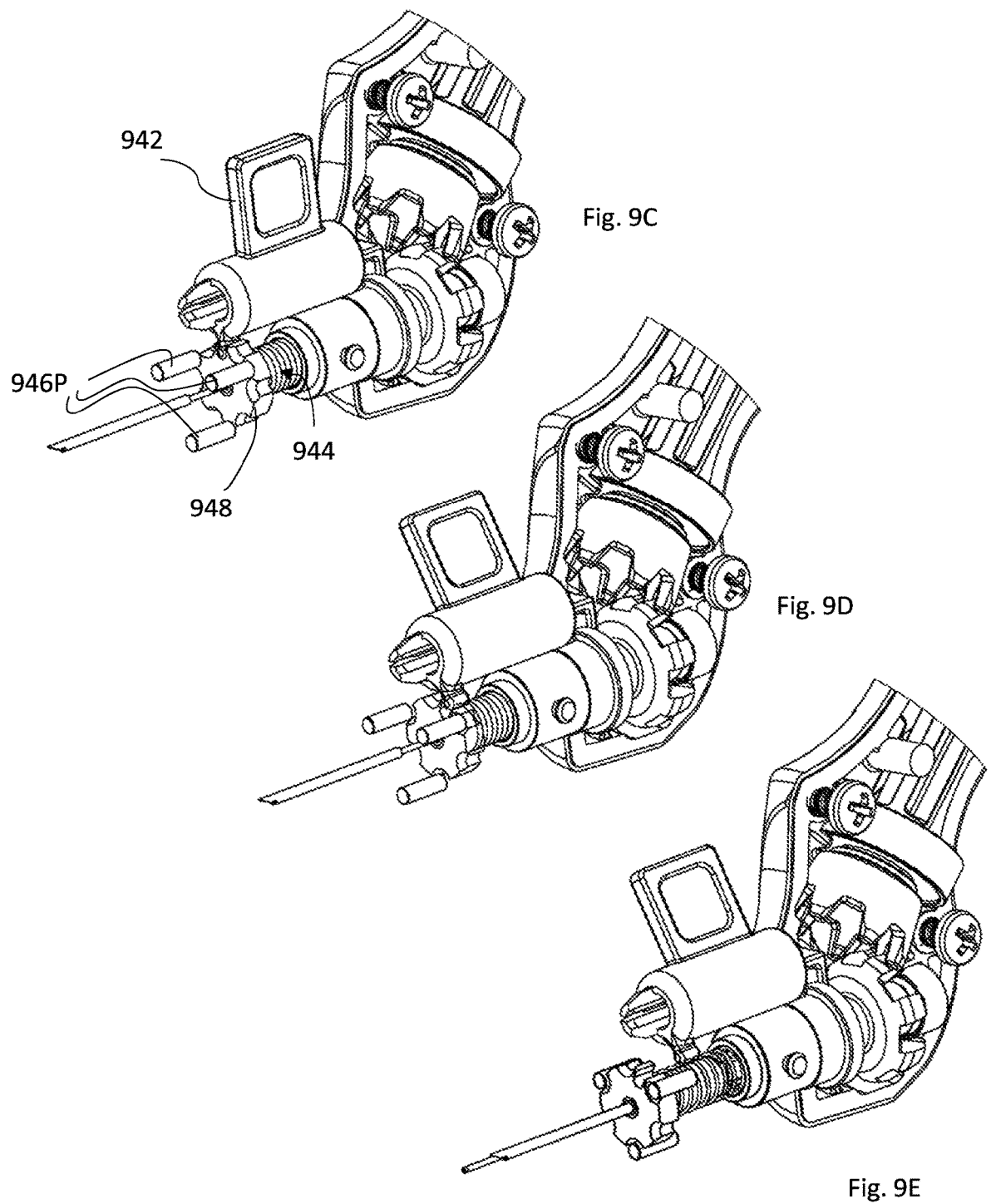

Reference is made to FIGS. 9A to 9E illustrating another non-limiting example of a movement mechanism configured for advancement of the inner member under constant or substantially constant force, e.g. 5-6N (with tolerance of about 1N). FIGS. 9A and 9B show the whole device 900. As shown, the device 900 includes outer member 910 and inner member 920 mounted on a handle 950 via a movement mechanism 940. FIGS. 9A, 9C and 9D show the device during the positioning phase, i.e. when the outer member is moved forwardly to pierce one or more tissue layers and/or until being inserted and anchored in the target tissue layer (all by manual pushing of the handle by the operating surgeon). FIGS. 9B and 9E show the device during the channeling phase, i.e. when the inner member 920 is rotated, by an electric motor, and advanced distally to create the channel in the target tissue layer.

The movement mechanism 940 includes a knob 942, a spring 944, a floating disk 948 and a housing 946 including three pins 946P firmly received therein in a spaced-apart relationship matching the floating disk's teeth. The outer member is permanently attached to the housing 946 such that it does not move relative to the handle 950, and the outer member's axial movement is generated only by the operating surgeon by pushing the handle forwards and pulling it backwards.

During the positioning phase, as shown in FIG. 9C, the spring 944 is compressed applying a distal pushing force on the floating disk 948. However, the floating disk is kept stationary while the knob 942 is engaged with the floating disk 948 preventing from moving.

As shown in FIG. 9D, after the outer member is inserted and anchored in the sclera, the operating surgeon turns on the electrical motor to cause rotation of the inner member, then turns the knob to the right or left and releases the floating disk 948. Once the floating disk is released it turns and is pushed distally by the spring 944 which starts to relax, the floating disk engages with the pins 946P, as shown in FIG. 9E. The floating disk 948 is also axially attached to a base of the inner member, such that the floating disk's distal movement under the constant relaxing force of the spring 944 causes the rotating inner member to move distally under a constant force until the floating disk reaches the distal side of the housing 946 and the axial movement stops. Additionally, though not specifically illustrated, the movement mechanism may include a latch configured to lock the knob 942, and only when the latch is released by the operating surgeon, the retraction movement of the inner member occurs.

Figure 10A:
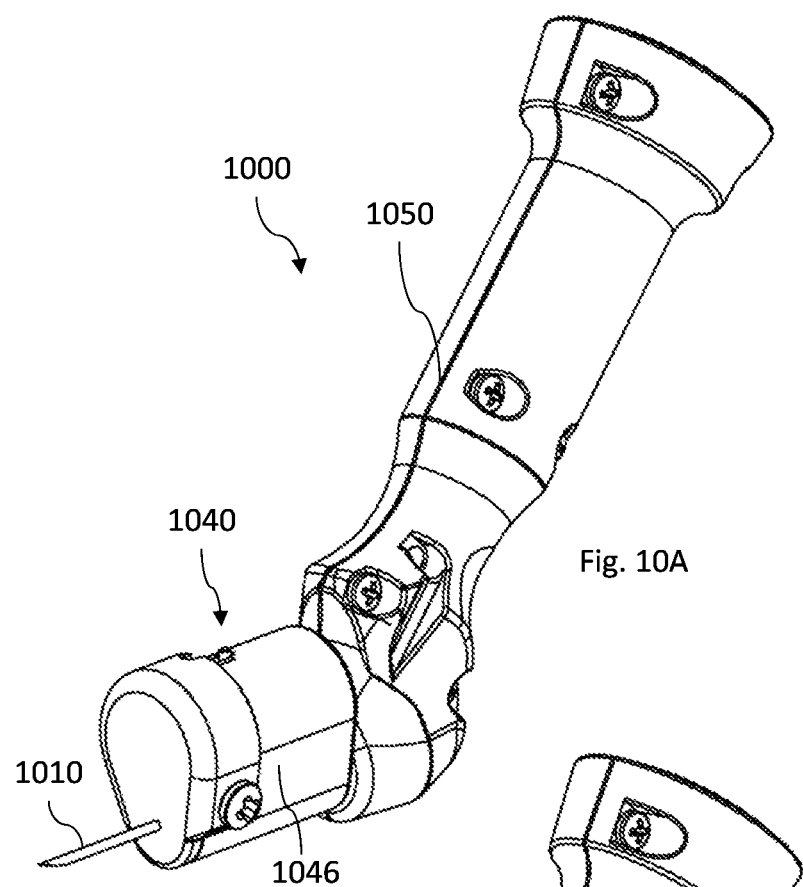
FIGS. 10A-10D illustrate another non-limiting example of automatic movement mechanism according to the invention.
Figure 10B:
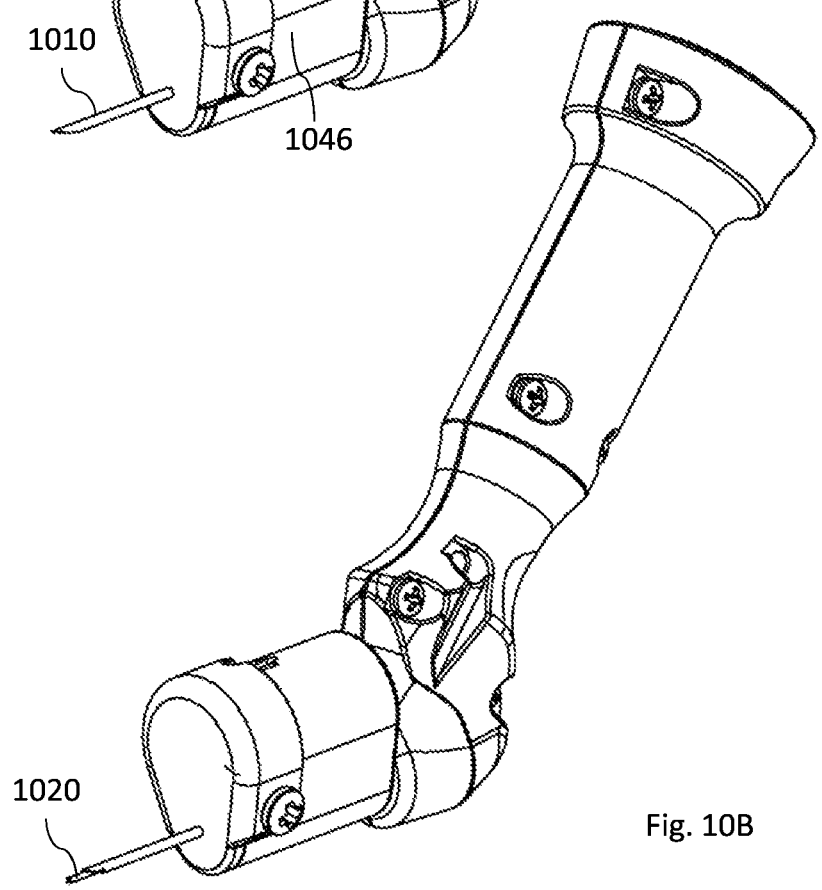
Figure 10C:
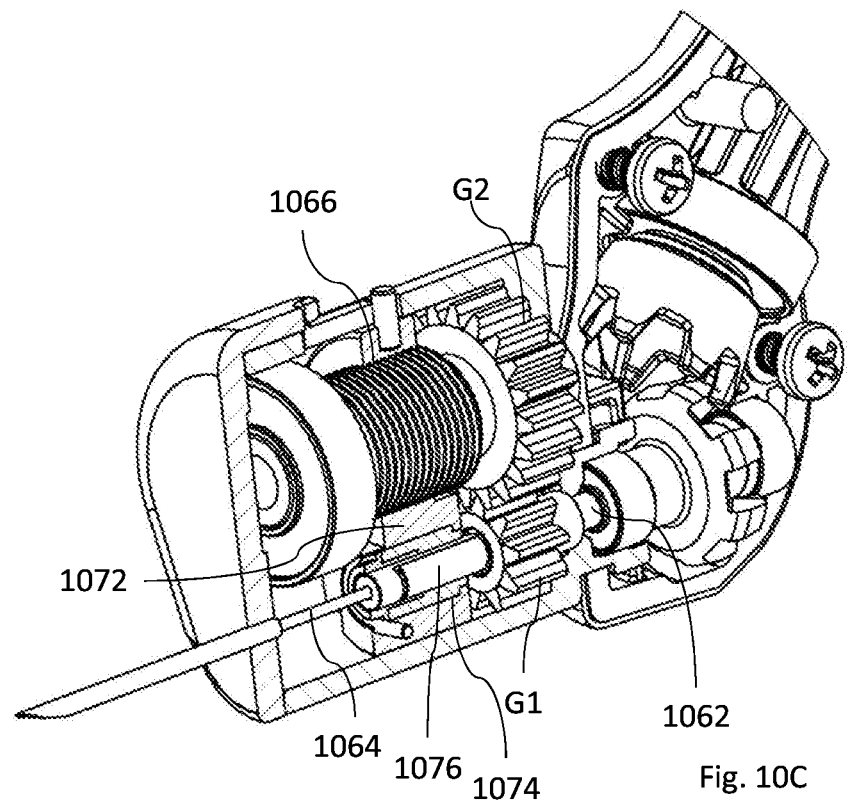
Figure 10D:
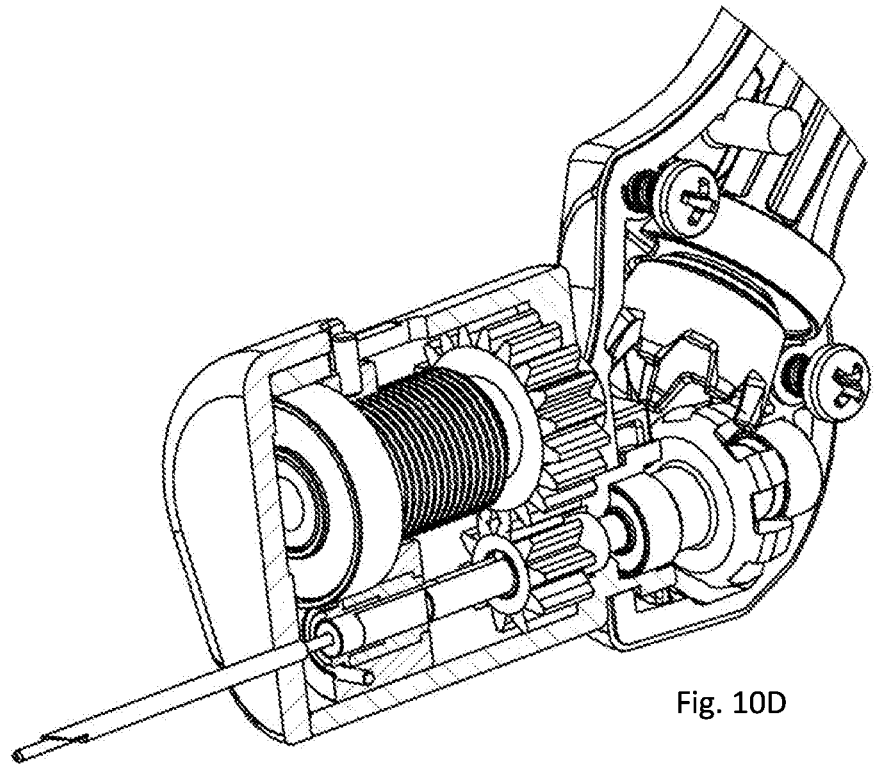

Reference is made to FIGS. 10A to 10D illustrating another non-limiting example of a movement mechanism configured for advancement of the inner member under constant rate. FIGS. 10A and 10B show the whole device 1000. As shown, the device 1000 includes outer member 1010 and inner member 1020 mounted on a handle 1050 via a movement mechanism 1040. FIGS. 10A and 10C show the device during the positioning phase, i.e. when the outer member is moved forwardly to pierce one or more tissue layers and/or until being inserted and anchored in the target tissue layer (by manual pushing of the handle by the operating surgeon). FIGS. 10B and 10D show the device during the channeling phase, i.e. when the inner member 1020 is rotated, by an electric motor, and advanced distally to create the channel in the target tissue layer.

The movement mechanism 1040 is configured for automatic rotation and advancement of the inner member. The rotation and advancement movements can be executed by the same or different motors. Additionally, the rate of the rotation and advancement movements can be the same or different, regardless of whether one or two separate motors are employed.

As shown in FIGS. 10C and 10D, the movement mechanism 1040 includes two gears G1 and G2. Gear G1 receives, at a first rate (e.g. 100-500 rounds per minute (RPM)), the rotational power delivered by the motor (which is not shown). Gear G1 rotates with the inlet shaft 1062 which is constantly connected to Gear G1 and is responsible for the rotational movement of the inner member 1020. The inner member is connected to the inlet shaft 1062 via an outlet shaft 1064 which rotates together with the inlet shaft 1062 yet it can move axially with respect to the inlet shaft 1062. Gear G2 is engaged with gear G1 such that it rotates according to a predetermined ratio between G1 and G2. Gear G2 is responsible for the axial movement of the inner member as shown in FIG. 10D. Gear G2 is connected constantly to a parallel shaft 1066 that has a built-in driving thread, as shown, such that the rotational movement of the Gear G2 and the parallel shaft 1066 is translated to an axial movement, of a driving nut 1072, via the built-in driving thread. The axial movement of the inner member is controlled by the housing's 1046 length along the axial direction. The driving nut 1072 is driven by the rotation of the parallel shaft 1066, via the built-in thread, such that it moves to the distal direction and forces the outlet shaft 1064 distally with it. A bearing 1074 between the driving nut 1072 and outlet shaft 1064 enables the outlet shaft to rotate as it moves axially while a fork-like shaft 1076 enables the outlet shaft to continue turning along the axial distal travel.

The invention claimed is:

1. A medical device configured and operable for removing a defined shape of soft tissue from a target tissue layer in an eye thereby creating a matching channel with predetermined geometry and orientation between two side walls of the target tissue layer to enable drainage of fluid from the eye through the channel, the device comprising coaxial outer and inner elongated members extending along axis X;

said outer member comprising an open distal side and a first distal part configured for sticking to said target tissue layer during forward axial movement;

said inner member comprising:

a second distal part configured to rotate and project distally, along said axis X, through said open distal side of the outer member, the second distal part being open at a distal end thereof and comprising a round cutting edge having a first diameter, the cutting edge being configured to attach to said target tissue layer and cut said shape of the soft tissue from the target tissue layer while rotating and progressing, thereby creating said channel formed as a hole through the target tissue layer, and retract backwardly into said outer member, and a chamber extending proximally from said open second distal part to a proximal end of the chamber, the chamber being configured to retain and store said removed shape of soft tissue in said removed shape of soft tissue's intact form, thereby providing a validation and authentication to the volume and shape of the corresponding channel created inside the target tissue layer wherein said chamber has one of the following configurations:
a) the chamber has dimensions matching said predetermined shape of the soft tissue, said predetermined shape of the soft tissue is cylindrical and has a length of about 1.5 mm and a diameter of between about 0.1 mm and about 0.2 mm;
b) the chamber has a length of at least the length of the removed tissue and has a chamber diameter smaller than said first diameter at a distal end of the chamber and which increases continuously towards the proximal end of the chamber; or
c) the chamber has a length of at least the length of the removed tissue and has a constant chamber diameter being equal to said first diameter, and wherein said first diameter is between about 0.1 mm to about 0.2 mm.

2. The medical device according to claim 1, wherein said first distal part is configured for penetrating at least one other tissue layer preceding said target tissue layer during said forward axial movement, said first distal part comprises a tissue piercing tip at a distal end of the first distal part configured and operable to penetrate said at least one other tissue layer and said target tissue layer and a proximal portion at a proximal side of the first distal part configured and operable to penetrate said at least one other tissue layer and to stop at said target tissue layer, thereby sticking said outer member in the target tissue layer.

3. The medical device according to claim 2, wherein said first distal part has a predefined length such that said tissue piercing tip does not exit distally from said target tissue layer.

4. The medical device according to claim 2, wherein said proximal portion is a rim of said outer member, formed by cutting a section of wall of the outer member along said axis X.

5. The medical device according to claim 1, having at least one of the following configurations:

a) said inner member is fixedly attached to and housed within said outer member during said forward axial movement of said outer member; or
b) said outer member is manually moved during said forward axial movement until said sticking of said outer member in said target tissue layer.

6. The medical device according to claim 1, having one of the following configurations:
a) said inner member, while rotating, is manually moved along said axis X to create the channel;
b) the device comprising a constant-force moving mechanism configured and operable to move said inner member, while rotating, along said axis X under a constant force;
c) the device comprising a constant rate moving mechanism configured and operable to move said inner member, while rotating, along said axis X with a constant rate; or
d) the device comprising an electric motor configured and operable for axially moving and or rotating said inner member.

7. The medical device according to claim 1, wherein said inner member comprises an elongated round body extending along the longitudinal axis X and has a uniform outer diameter at a proximal side thereof, said first diameter of the round cutting edge being smaller than said outer diameter and said second distal part has a continuously decreasing outer diameter towards the distal end.

8. The medical device according to claim 1, wherein said inner member comprises a tissue trapper comprising a slit formed in wall of the body of inner member along at least part of said chamber, said slit is formed by one of the following: a) tangential cutting of the wall of the body of inner member, said device thereby further comprising an outer chamber located between the inner and outer members, b) radial cutting of the wall of the body of inner member.

9. The medical device according to claim 1, wherein said rotating of said second distal part comprises clockwise and anti-clockwise reciprocal movement.

10. The medical device according to claim 1, wherein said first distal part of the outer member is formed by cutting the outer member in the direction of the axis X along a curved line chosen to provide smooth penetration, at a distal segment of the first distal part, with increasing resistance-to-progression force, at a proximal segment of the first distal part.

11. The medical device according to claim 1, wherein said predetermined geometry and orientation of the channel are selected to enable pressure regulation of a treated eye over a predetermined time period.

* * * * *